United States Patent [19]

Justice et al.

[11] Patent Number: 5,364,842

[45] Date of Patent: Nov. 15, 1994

[54] METHOD OF PRODUCING ANALGESIA

[75] Inventors: Alan Justice, Sunnyvale; Tejinder Singh, Palo Alto; Kishor C. Gohil, Richmond; Karen L. Valentino, San Carlos, all of Calif.

[73] Assignee: Neurex Corporation, Menlo Park, Calif.

[21] Appl. No.: 81,863

[22] Filed: Jun. 23, 1993

Related U.S. Application Data

[63] Continuation of Ser. No. 814,759, Dec. 30, 1991, abandoned.

[51] Int. Cl.$^5$ .................... A61K 37/00; A61K 37/02; C07K 5/00; C07K 7/00
[52] U.S. Cl. .................... 514/12; 530/300; 530/324
[58] Field of Search .................... 514/12; 530/300, 324

[56] References Cited

FOREIGN PATENT DOCUMENTS 9107980 6/1991 WIPO .................... A61K 37/02

OTHER PUBLICATIONS

Carta et al., Chemical Abstracts, vol. 114, No. 19, Abst No.: 178244t.
Antkiewicz-Michaluk et al., Chemical Abstracts, vol. 115, No. 21, Abst. No.: 223387a.
Feldman et al., FEBS Lett., vol. 214, No. 2, pp. 295–300 Apr. 1987.
Olivera et al., Biochemistry, vol. 26, pp. 2086–2090, 1987.
Basilico, L., et al., "Influence of ω–conotoxin on morphine analgesia and withdrawal syndrome in rats," *European Journal of Pharmacology* 218(1):75–81 (1992).
Basilico, L., et al., "Interaction of Opiates with ω–Conotoxin in Guinea Pig Ileum in Vitro," *Pharmacological Research* 21(1);65 (1989).
Benedek, G., and M. Sziksza, "Potentiation of thermoregulatory and analgesic effects of morphine by calcium antagonists," *Pharmacological Research Communications* 16(10):1009 (1984).
Ben-Sreti, M. M., et al., "Effects of elevated calcium and calcium antagonists on 6,7-benzomorphan-induced analgesia," *European Journal of Pharmacology*, 90:385–391 (1983).
Contreras, E., et al., "Calcium channel antagonists increase morphine-induced analgesia and antagonize morphine tolerance," *European Journal of Pharmacology* 148:463–466 (1988).
Del Pozo, E., et al., "Analgesic effects of several calcium channel blockers in mice," *European Journal of Pharmacology* 137:155–160 (1987).
Hoffmeister, F., and D. Tettenborn, "Calcium agonists and antagonists of the dihydropyridine type: Antinociceptive effects, interference with opiate–μ–receptor agonists and neuropharmacological actions in rodents," *Psychopharmacology* 90:299–307 (1986).
Kavaliers, M., "Stimulatory influences of calcium channel antagonists on stress-induced opioid analgesia and locomotor activity," *Brain Research* 408:403–407 (1987).
Keith, R. A., et al., "Neomycin and ω–conotoxin GVIA interact at a common neuronal site in peripheral tisuses," *J. Auton. Pharmac.* 10: 139–151 (1990).

(List continued on next page.)

Primary Examiner—Lester L. Lee
Assistant Examiner—A. M. Davenport
Attorney, Agent, or Firm—Peter J. Dehlinger; Carol A. Stratford

[57] ABSTRACT

A method of producing analgesia and enhancing opiate analgesia is disclosed. The method includes administering TVIA (SNX-185) or MVIIA (SNX-111) omega-conopeptide, or derivative thereof which is characterized by its ability to (a) inhibit voltage-gated calcium channels selectively in neuronal tissue, as evidenced by the peptide's ability to inhibit electrically stimulated contraction of the guinea pig ileum, and (b) bind to omega-conopeptide MVIIA binding sites present in neuronal tissue.

4 Claims, 20 Drawing Sheets

OTHER PUBLICATIONS

Knaus, H-G., et al., "Neurotoxic aminoglycoside antibiotics are potent inhibitors [$^{125}$I]-Omega-Conotoxinc GVIA binding to guinea-pig cerebral cortex membranes," *Naunyn-Schmiedeberg's Arch Pharmacol* 336: 583–586 (1987).

Konno, F., and I. Takayanagi, "Relationship between synaptosomal calcium uptake and antinociceptive action of morphine," *Japan J. Pharmacol.* 33:619–626 (1983).

Lux, F., et al., "Interaction of Morphine with Intrathecally Administered Calcium and Calcium Antagonists: Evidence for Supraspinal Endogenous Opioid Mediation of Intrathecal Calcium-Induced Antinociception in Mice," *J. Pharmacol. Exp. Therapeutics* 246:500 (1988).

Mackie, K., and B. Hille, "Cannabinoids inhibit N-type calcium channels in neuroblastoma-glioma cells," *Proc. Natl. Acad. Sci. USA* 89:3825–3829 (1992).

Ocana, M., and J. M. Baeyens, "Analgesic effects of centrally administered aminoglycoside antibiotics in mice," *Neuroscience Letters* 126:67–70 (1991).

Prado, W. A., et al., "Antinociception induced by intraperitoneal injection of gentamicin in rats and mice," *Pain* 41:365–371 (1990).

Wagner, J. A., et al., "Aminoglycoside effects on voltage-sensitive calcium channels and neurotoxicity," *New England J. Medicine* 317(26): 1669 (1987).

Welch, S. P., and W. L. Dewey, "A Characterization of the Antinociception Produced by Intracerebroventricular Injection of 8-(N,N-Diethylamino)Octyl-3,4,5-Trimethoxybenzoate in Mice," *J. Pharmacol. Exp. Therapeutics* 239:320 (1986).

Woodward, J. J., et al., "Differential sensitivity of synaptosomal calcium entry and endogenous dopamine release to $\omega$-conotoxin," *Brain Research* 475:141–145 (1988).

|  | 1 | 5 | 10 | 15 | 20 | 25 | 30 |
|---|---|---|---|---|---|---|---|
| MVIIA/SNX-111 | C K G K G A K C S R L M Y D C C T G S C - R - S G K - C |
| MVIIB/SNX-159 | C K G K G A S C H R T S Y D C C T G S C N R - - G K - C |
| GVIA/SNX-124 | C K S X G S S C S X T S Y N C C R - S C N X Y T - K R C - - Y |
| GVIIB/SNX-178 | C K S X G T X C S R G M R D C C T - S C L L Y S N K - C R R Y |
| RVIA/SNX-182 | C K P X G S X C R V S S Y N C C S - S C K S Y - N K K C G |

Fig. 1

|  | 1 |  |  |  |  | 5 |  |  |  |  | 10 |  |  |  |  | 15 |  |  |  |  | 20 |  |  |  |  | 25 |  |  |  |  | 30 |
|---|---|---|---|---|---|---|---|---|---|---|---|---|---|---|---|---|---|---|---|---|---|---|---|---|---|---|---|---|---|---|---|---|
| SVIA/SNX-157 | C | R | S | S | G | S | X | C | G | V | T | S | I | - | C | C | - | G | R | C | - | - | Y | R | G | K | - | C | T |
| TVIA/SNX-185 | C | L | S | X | G | S | C | S | X | T | S | Y | N | C | C | R | - | S | C | N | X | Y | S | - | R | K | C | R |
| SVIB/SNX-183 | C | K | L | K | G | Q | S | C | R | K | T | S | Y | D | C | C | S | G | S | C | G | R | - | S | G | K | - | C |
| MVIIC/SNX-230 | C | K | G | K | G | A | P | C | R | K | T | M | Y | D | C | C | S | G | S | C | G | R | - | R | G | K | - | C |
| SNX-231 | C | K | G | K | G | A | X | C | R | K | T | M | Y | D | C | C | S | G | S | C | G | R | - | R | G | K | - | C |

Fig. 1 (con't)

Fig. 2

```
                1           5              10              15              20              25
MVIIA           C  K  G  K  G  A  K  C  S  R  L  M  Y  D  C  C  T  G  S  C  R  S  G  K  C-NH₂
(SNX-111)
SNX-190         -  -  -  -  A  -  -  -  -  -  -  -  -  -  -  -  -  -  -  -  -  -  -  -  -    NH₂
SNX-191         -  -  A  -  -  -  -  -  -  -  -  -  -  -  -  -  -  -  -  -  -  -  -  -  -    NH₂
SNX-193         -  -  -  -  -  -  -  -  -  -  -  -  -  -  -  -  -  -  -  -  -  -  -  -  -    G-OH
SNX-194         -  -  -  -  -  -  -  -  -  -  -  -Nle- -  -  -  -  -  -  -  -  -  -  -  -    NH₂
SNX-195         -  -  -  -  -  -  -  -  -  -  -  -  -  -  -  -  -  -  -  -  -  -  -  A  -    NH₂
SNX-196     N-  -  -  -  -  -  -  -  -  -  -  -  -  -  -  -  -  -  -  -  -  -  -  -  -  -    G-OH
SNX-197    NS-  -  -  -  -  -  -  -  -  -  -  -  -  -  -  -  -  -  -  -  -  -  -  -  -  -    NH₂
SNX-198         -  -  -  -  -  -  -  -  -  -  -  -  -  -  -  -  -  -  -  -  A  -  -  -  -    NH₂
SNX-200         -  -  -  -  -  -  A  -  -  -  -  -  -  -  -  -  -  -  -  -  -  -  -  -  -    NH₂
SNX-201         -  -  -  -  -  -  -  -  R  K  T  S  -  -  -  -  -  -  -  -  -  -  -  -  -    NH₂
```

```
SVIB      C L K G Q S C R K T S Y D C C S G S C G R S G K C NH₂
(SNX-183)         └─────────────┘   └─┘       └─────────────┘
                                    └───────────────────────┘

SNX-202   - - - - - - - - - - - - - S R L M - - - - - - - NH₂

TVIA      C L S X G S S C S X T S Y N C C R S C N X Y S R K C R NH₂
(SNX-185)         └─────────────┘   └─┘     └─────────────────┘
                                    └─────────────────────────┘

SNX-207   - - - - - - - - - - - - - - R L M - - - - - - - - NH₂
```

Fig. 2 (con't)

Fig. 5A
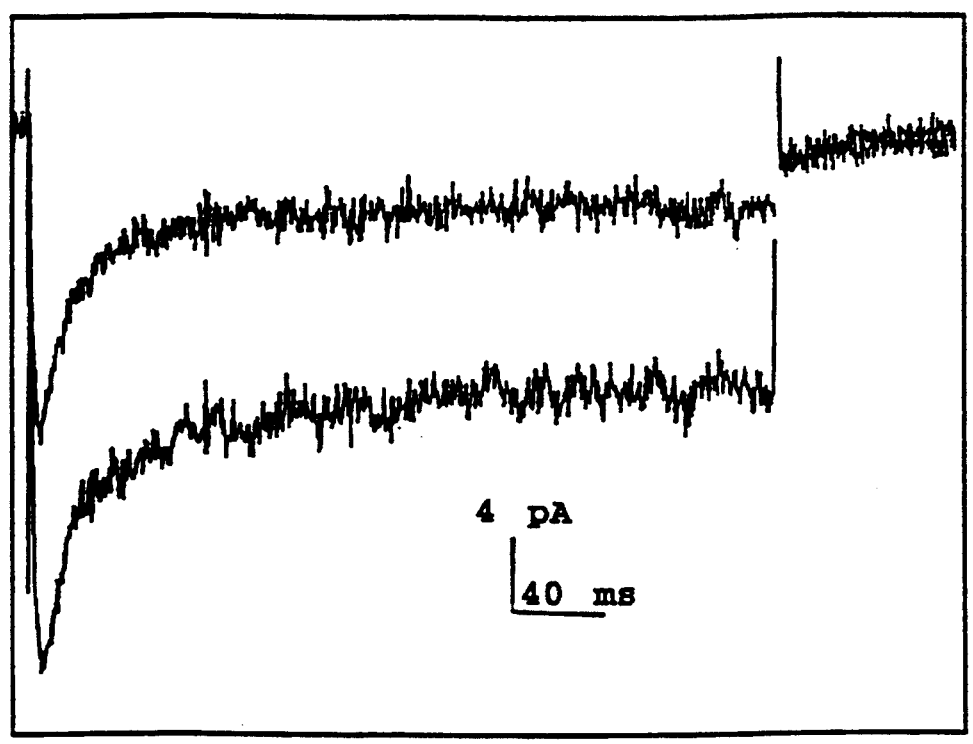
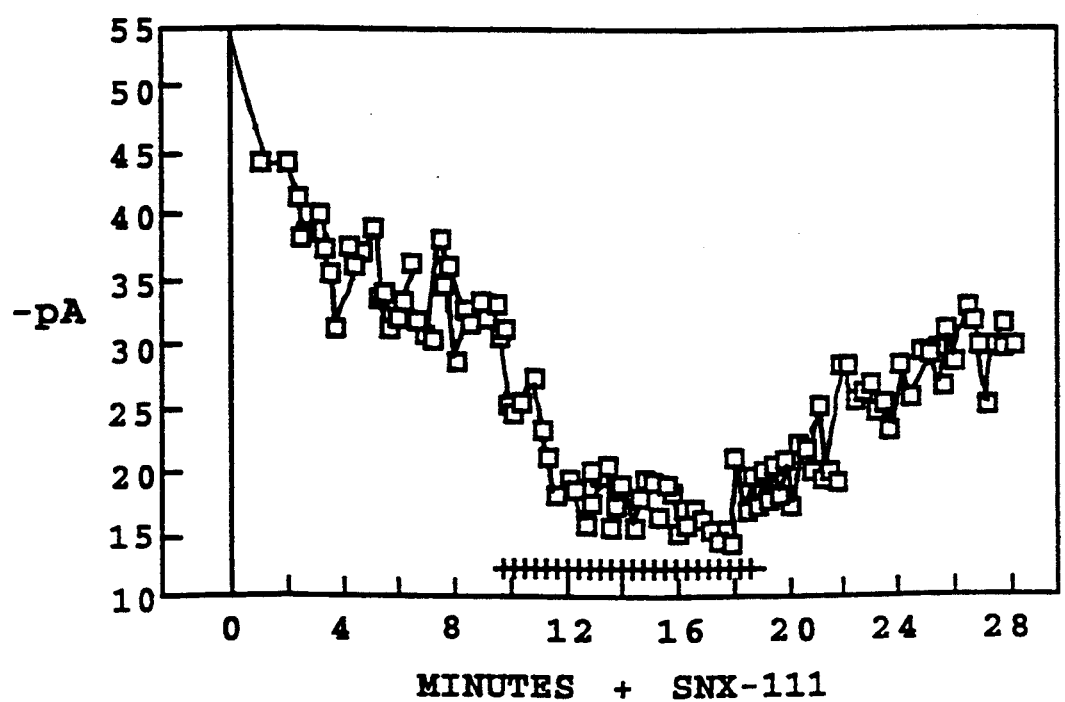
Fig. 5B

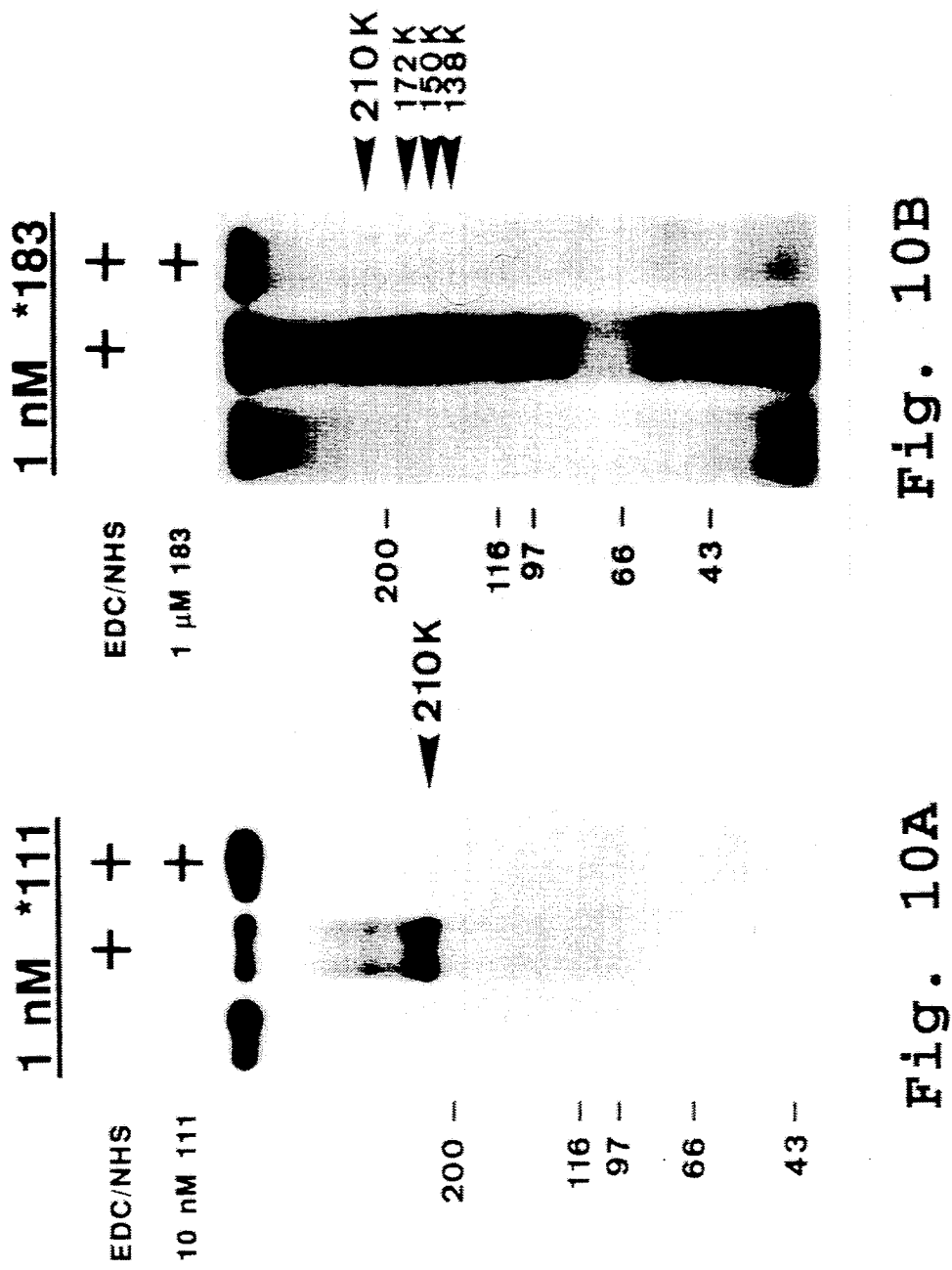

*111
Fig. 12A ROSTRAL SECTIONS
Fig. 12B CAUDAL SECTIONS
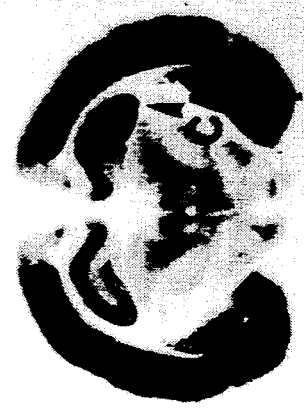
*111 + excess 111
Fig. 12C
Fig. 12D

ROSTRAL SECTIONS CAUDAL SECTIONS

SN

*183

*183
+
excess
183

|  | 1 | 5 | 10 | 15 | 20 | 25 | 30 |
|---|---|---|---|---|---|---|---|
| I. | | | | | | | |
| MVIIA | C K G K G A K C S R L M Y D C C T G S C - R - S G K - C | | | | | | |
| MVIIB | C K G K G A S C H R T S Y D C C T G S C N R - G K - C | | | | | | |
| II. | | | | | | | |
| TVIA | C L S X G S S C S X T S Y N C C R - S C N X Y S R K - C R | | | | | | |
| SNX-207 | C L S X G S S C S R L M Y N C C R - S C N X Y S R K - C R | | | | | | |
| SNX-236 | C L S X G S S C S R L M Y N C C R - S C N P Y S R K - C R | | | | | | |
| III. | | | | | | | |
| RVIA | C K P X G S X C R V S S Y N C C S - S C K S Y - N K K C G | | | | | | |
| SVIA | C R S S S X. C G V T S I - C C - C G R C - Y R G K - C T | | | | | | |
| GVIIA | C K S X G T X C S R G M R D C C T - S C L L Y S N K - C R R Y D | | | | | | |
| SVIB | C K L K G Q S C R K T S Y D C C S G S C G R - S G K - C | | | | | | |
| MVIIC | C K G K G A P C R K T M Y D C C S G S C G R - R G K - C | | | | | | |
| SNX-231 | C K G K G A X C R K T M Y D C C S G S C G R - R G K - C | | | | | | |

Fig. 14

METHOD OF PRODUCING ANALGESIA

This application is a continuation of application Ser. No. 07/814,759, filed Dec. 30, 1991, and now abandoned.

FIELD OF THE INVENTION

The present invention relates to methods of producing analgesia and enhancing opiate analgesia, particularly in the treatment of pain.

REFERENCES

Ahmad, S., and Miljanich, G. P. (1988). Brain Research 453:247–256.

Basilico, L., Parenti, M., Frevola, L., and Giagnon, G. (1989). Pharmacol. Res. 21:65–66.

Bennett, J. P. et al. (1983) *Neurotransmitter Receptor Binding* pp. 61–89; Raven Press, New York.

Ben-Sreti, M. M., Gonzalez, J. P. and Sewell, R. D. E. (1983) Eur. J. Pharmacol. 90:385–391.

Contreras, E., Tamayo, L., and Amigo, M. (1988) Eur. J. Pharmacol. 148:463–466.

Fitzgerald, M. (1989) TINS 12(3):86–87.

Gray, W., Olivera, B., and Cruz, L. (1988), Annual Review of Biochemistry 57:665–700.

Hartley, D. and Choi, D. (1989), The Journal of Pharmacology and Experimental Therapeutics 250:752–758.

Kenakin, T. P. (1987) *Pharmacologic Analysis of Drug-Receptor Interaction*, Raven Press, N.Y.

McCleskey, E. W. et al., Proc. Natl. Acad. Sci. U.S.A. 84:4327–4331 (1987).

McGeer, P. L., Eccles, J. C. and McGeer, E. G. (1987) *Molecular Neurobiology of the Mammalian Brain* Plenum Press, N.Y.

Nowycky, M. C., Fox, A. P., and Tsien, R. W., Nature (London), 316:440–443 (1985).

Olivera, B., McIntosh, M., Cruz, L., Luque, F., and Gray, W. (1984), Biochemistry 23:5087–5090.

Paxinos, G., and Watson, C. (1986). *The Rat Brain in Stereotaxic Coordinates*, 2nd Edition.

Ritchie, J. M. and Greene, N. M. (1990) in *Goodman and Gilman's The Pharmacological Basis of Therapeutics*, (Eighth Edition) Pergamon Press (New York) Chapter 15, pp. 311–331.

Sher, E. et al. (1991) FASEB J. 5:2677–2683.

Takemura, M., et al. (1988). Neuroscience Res. 5:405–416.

Yaksh, T. L. and Noueihed, R. (1985) Ann. Rev. Pharmacol. Toxicol 25:433–462.

BACKGROUND OF THE INVENTION

Chronic or intractable pain, such as may occur in conditions such as degenerative bone diseases and cancer, is a debilitating condition which is treated with a variety of analgesic agents, and often opioid compounds, such as morphine.

In general, brain pathways governing the perception of pain are still incompletely understood. Sensory afferent synaptic connections to the spinal cord, termed "nociceptive pathways" have been documented in some detail. In the first leg of such pathways, C- and A-fibers which project from peripheral sites to the spinal cord carry nociceptive signals. Polysynaptic junctions in the dorsal horn of the spinal cord are involved in the relay and modulation of sensations of pain to various regions of the brain, including the periaqueductal grey region (McGeer). Analgesia, or the reduction of pain perception, can be effected directly by decreasing transmission along such nociceptive pathways. Analgesic opiates are thought to act by mimicking the effects of endorphin or enkephalin peptide-containing neurons, which synapse presynaptically at the C- or A-fiber terminal and which, when they fire, inhibit release of substance P. Descending pathways from the brain are also inhibitory on C- and A-fiber firing.

Opioids (opiates) such as morphine, while effective in producing analgesia, may induce tolerance in a subject, so that increasing doses are required to achieve a satisfactory effect. At high doses, such compounds produce side effects, including respiratory depression, which can be life threatening. Moreover, such compounds are also liable to produce physical dependence in a subject. Dependence appears to be related to the dose of opioid taken and the period of time over which it is taken. Therefore, compounds which serve as either a replacement for or as an adjunct to opioid treatment in order to decrease the dosage of analgesic compound required, have utility in the treatment of pain, particularly pain of the chronic, intractable type.

Although calcium blocking agents, including a number of L-type calcium channel antagonists, have been tested as adjunct therapy to morphine analgesia, positive results are attributed to direct effects on calcium availability, since calcium itself is known to attenuate the analgesic effects of certain opioid compounds (Ben-Sreti). EGTA, a calcium chelating agent, is effective in increasing the analgesic effects of opioids. Moreover, in some cases, results from tests of calcium antagonists as adjunct therapy to opioids have been contradictory; some L-type calcium channel antagonists have been shown to increase the effects of opioids, while others of these compounds have been shown to decrease opioid effects (Contreras).

U.S. Pat. No. 5,051,403 describes the use of omega-conopeptides having defined binding/inhibitory properties in the treatment of ischemia-related neuronal damage. In the present invention, it has been found that omega-conopeptides having related inhibitory and binding activities enhance the effects of opioid compounds in producing analgesia in mammalian subjects. In addition, these compounds may also produce analgesia in the absence of opioid treatment.

SUMMARY OF THE INVENTION

The invention includes, in one aspect, a method of enhancing the analgesic effect produced by administration of opiates to a mammalian subject. In another aspect, the invention includes a method of producing analgesia in a mammalian subject. The methods include administering to the subject, an omega-conopeptide which is either TVIA (SNX-185), MVIIA (SNX-111) or a derivative thereof which is effective (a) to inhibit voltage-gated calcium channels selectively in neuronal tissue, as evidenced by the peptide's ability to inhibit electrically stimulated contraction of the guinea pig ileum, and (b) to bind to omega-conopeptide MVIIA binding sites present in neuronal tissue. The omega-conopeptide is administered at a dose effective to produce analgesia or enhance the analgesic effect of the opiate.

In a preferred embodiment, the activities of the omega-conotoxin in calcium channel inhibition and in binding to the MVIIA binding site are within the ranges of such activities of omega-conotoxins MVIIA and TVIA, and the omega-conopeptide is administered intrathecally.

These and other objects and features of the present invention will become more fully apparent when the following detailed description of the invention is read in conjunction with the accompanying drawings.

BRIEF DESCRIPTION OF THE DRAWINGS

FIG. 1 shows primary sequences of several natural omega-conopeptides, MVIIA/SNX-111 (SEQ ID NO: 01), MVIIB/SNX-159 (SEQ ID NO: 02), GVIA/SNX-124 (SEQ ID NO: 03), GVIIA/SNX-178 (SEQ ID NO: 04), RVIA/SNX-182 (SEQ ID NO: 05), SVIA/SNX-157 (SEQ ID NO: 06), TVIA/SNX-185 (SEQ ID NO: 07), SVIB/SNX-183 (SEQ ID NO: 08), MVIIC/SNX-230 (SEQ ID NO: 29) and SNX-231 (SEQ ID NO: 30);

FIG. 2 shows several analog omega-conopeptides SNX-190 (SEQ ID NO: 09), SNX-191 (SEQ ID NO: 10), SNX-193 (SEQ ID NO: 11), SNX-194 (SEQ ID NO: 12), SNX-195 (SEQ ID NO: 13), SNX-196 (SEQ ID NO: 14), SNX-197 (SEQ ID NO: 15), SNX-198 (SEQ ID NO: 16), SNX-200 (SEQ ID NO: 17), SNX-201 (SEQ ID NO: 18), SNX-202 (SEQ ID NO: 19), SNX-207 (SEQ ID NO: 20), and their relationships to SNX-111 (SEQ ID NO: 01), SNX-185 (SEQ ID NO: 07) or SNX-183 (SEQ ID NO: 08);

FIG. 5A shows voltage-gated calcium current traces induced by a voltage step from −70 to −20 mV in human neuroblastoma cells (IMR-32) in the absence (lower trace) and presence (upper tracing) of 150 nM SNX-111;

FIGS. 5B and 5C show plots of absolute values of peak inward current measured every 15 seconds in IMR-32 cells, elicited by pulses from −70 to 0 or −10 mV, versus time, where addition of compounds SNX-111 (5B) or SNX-111, SNX-183 (5C), and cadmium to the bathing medium are indicated by hatch marks just above the ordinate;

FIG. 10 (A and B) shows SDS-PAGE autoradiograms of rat synaptosomal membranes having covalently bound radioiodinated OCT MVIIA (SNX-111)(A) or covalently bound radioiodinated OCT SVIB (SNX-183)(B) added to the membranes in the presence (lanes c and f) or absence (lanes a,b and d,e) of non-radiolabeled OCT, where lanes a and d are control preparations in which no cross-linking agent was added;

FIGS. 12A, 12B, 12C, 12D, 12E, 12F, 12G and 12H shows autoradiograms of the distributions of [$^{125}$I]-SNX-111 12(A,B,C,D) and [$^{125}$I]-SNX-183 12(E,F,G,H) binding to coronal rat brain rostral 12(A,C,E,G) and caudal 12(B,D,F,H) sections labeled in the absence of excess nonradioactive SNX-111 12(A,B) or SNX-183 12(E,F) or in the presence of excess non-radioactive SNX-111 12(C,D) or SNX-183 12(G,H), in which "CA" indicates the CA$_3$ region of the hippocampus and "SN" indicates the substantia nigra;

FIG. 14 shows omega-conopeptide groupings;

DETAILED DESCRIPTION OF THE INVENTION

I. Omega-conopeptides

Figure 3:
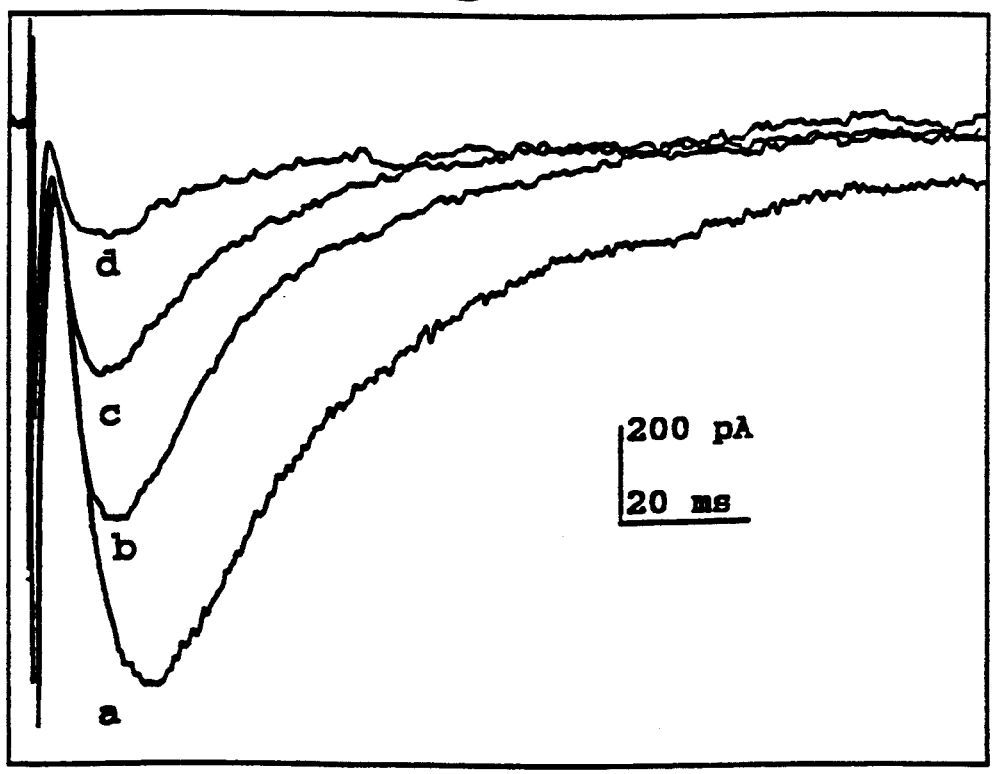
FIGS. 3A–3D show voltage-gated calcium current traces induced by a voltage step from −100 or −80 mV to −20 mV in untreated N1E-115 neuroblastoma cells (3A) and in neuroblastoma cells exposed to increasing concentrations of OCT MVIIA (SNX-111) (3B–3D)

Omega-conopeptides or, omega-conotoxins are peptide components of venoms produced by marine snails of the genus Conus, and which act as calcium channel blockers (Gray). About 500 species of cone snails in the Conus genus have been identified, and a variety of omega-conopeptides from several of these species have been isolated. The primary sequences of eight natural omega-conopeptides are shown in FIG. 1. Conventional letter initials are used for the amino acid residues, and X represents 4-hydroxyproline, also abbreviated 4Hyp. All of the peptides shown in the figure are amidated at their C-termini.

The peptides shown in FIG. 1 are identified by names which are commonly associated with either the naturally occurring peptide (single letter followed by a Roman numeral followed by a single letter), and by a synthetic designation (SNX-plus numeral). Either or both of these designations will be used interchangeably throughout the specification. For example, the peptide whose sequence is designated MVIIA/SNX-111 will be referred to herein as OCT MVIIA, or alternatively, SNX-111, the latter to signify that the compound used was synthesized, rather than isolated directly from the organism. Synthetic and naturally occurring peptides having the same sequence behave substantially identically in the assays and methods of treatment of the invention. The OCT MVIIA (SNX-111) and OCT GVIA (SNX-124) peptides also have the common names CmTx and CgTx, respectively. OCT MVIIC is an omega-conopeptide whose gene was cloned from a *Conus magus* venom clone cDNA expression library. Its sequence is represented by SNX-230 or SNX-231 (FIG. 1) depending on post-translational modification of the proline at position 7. All of the omega-conopeptides have three disulfide linkages connecting cysteine residues 1 and 4, 2 and 5, and 3 and 6, as indicated for the MVIIA peptide in FIG. 2. FIG. 2 shows analogs of natural OCT MVIIA, OCT TVIA, and OCT SVIB peptides which have been synthesized and tested in accordance with the invention. Standard single amino acid code letters are used in the figure; X=hydroxyproline; Nle=norleucine; $NH_2$ group at the C terminus indicates that the peptide is C-terminal amidated; G-OH indicates termination in an unmodified glycine residue.

A. Preparation of Omega-conopeptides

This section describes the synthesis, by solid phase methods, of several naturally occurring omega-conotoxin (OCT) peptides and additional omega-conopeptides which are used in the present invention.

Omega-conopeptides, such as those shown in FIGS. 1 and 2, can be synthesized by conventional solid phase methods, such as have been described (Olivera). Briefly, N-alpha-protected amino acid anhydrides are prepared in crystallized form and used for successive amino acid addition at the N-terminus. At each residue addition, the growing peptide (on a solid support) is acid treated to remove the N-alpha-protective group, washed several times to remove residual acid and to promote accessibility of the peptide terminus to the reaction medium. The peptide is then reacted with an activated N-protected amino acid symmetrical anhydride, and the solid support is washed. At each residue-addition step, the amino acid addition reaction may be repeated for a total of two or three separate addition reactions, to increase the percent of growing peptide molecules which are reacted. Typically, 1-2 reaction cycles are used for the first twelve residue additions, and 2-3 reaction cycles for the remaining residues.

After completing the growing peptide chains, the protected peptide resin is treated with liquid hydrofluoric acid to deblock and release the peptides from the support. For preparing an amidated peptide, the resin support used in the synthesis is selected to supply a C-terminal amide, after peptide cleavage from the resin. The three disulfide linkages in the peptides may be formed by air oxidation in the presence of dithiothreitol (DTT) at room temperature or at 4° C. over an extended reaction period. Alternatively, where the correct or desired bridging cannot be achieved by random oxidation, a chemically directed process may be used in which the bridges are formed sequentially, one bridge at a time. The following side-chain protecting groups could be used for each pair of cysteine residues: 4-methylbenzyl, ethylcarbamoyl, and acetamidomethyl. These protecting groups constitute an orthogonal set in which any one kind of protecting group can be removed under conditions that do not affect the other two.

The strategy used in this method involves removing one kind of protecting group from a pair of cysteine residues, followed by oxidation to form the first disulfide bridge. A second kind of protecting group is then removed, again followed by oxidation to form the second bridge. A third bridge, if needed, is formed in like manner.

The peptide can be isolated by an initial separation by gel filtration, to remove peptide dimers and higher molecular weight polymers, and also to remove undesired salts, such as guanidine hydrochloride, used in the oxidation reaction. The partially purified peptide is further purified by preparative HPLC chromatography, and the purity of the peptide confirmed by amino acid composition analysis.

B. In vitro Properties of Omega-conopeptides

1. Calcium Channel Antagonist Activity

Voltage-gated calcium channels are present in neurons, and in cardiac, smooth, and skeletal muscle and other excitable cells, and are known to play a variety of roles in membrane excitability, muscle contraction, and cellular secretion, such as in synaptic transmission (McCleskey). In neuronal cells, voltage-gated calcium channels have been classified by their electrophysiological as well as by their biochemical (binding) properties.

Electrophysiologically, these channels can be classified either as Low-voltage-activated (LVA) or High-voltage-activated (HVA). HVA channels are currently known to comprise at least three groups of channels, known as L-, N- and P-type channels (Nowycky, Sher). These channels can be distinguished electrophysiologically as well as biochemically on the basis of their pharmacology and ligand binding properties. Thus, dihydropyridines, diphenylalkylamines and piperidines bind to the $alpha_1$ subunit of the L-type calcium channel and block a proportion of HVA calcium currents in neuronal tissue, which are termed L-type calcium currents.

Omega-conotoxins also block a proportion of HVA calcium currents in neuronal tissue, and, in the presence of a maximally inhibitory quantity of dihydropyridine compound, substantially inhibit the remaining HVA currents in neuronal cells. These calcium currents are identified as N-type calcium currents, though recently a proposal that such currents be termed "omega" has been presented (Sher). Omega-conotoxins bind to a specific population of binding sites. Dihydropyridines and other L-type channel blockers do not displace omega-conotoxin binding, nor do omega-conotoxins displace binding of ligands to L-channels. Unlike L-type calcium channels, omega channels are found predominantly, although not exclusively, in nervous tissue (Sher).

One suitable system for testing inhibition (blockage) of N-type or omega HVA neuronal calcium channels is an isolated cell system, such as the mouse neuroblastoma cell line, strain N1E115 or the human neuroblastoma cell line IMR32. Membrane currents are conveniently measured with the whole cell configuration of the patch clamp method, according to the procedure detailed in Example 1. Briefly, a voltage clamp protocol was performed in which the cell potential was stepped from the holding potential of about −100 mV to test potentials that ranged from −60 mV to +20 mV, and the cell was held at the holding potential for 5 seconds between pulses.

FIG. 3 shows a typical inward calcium current elicited by a voltage step from −80 mV to −20 mV in the absence of OCT. In this, and most of the recordings shown, barium (Ba) replaced calcium (Ca) as the charge-carrier through the calcium channels in order to increase the signal (McCleskey). According to the procedure described in Example 1, an N1E115 neuroblastoma cell was bathed in saline with sodium replaced by N-methyl-D-glucamine (NMDG), and 10 mM Ba instead of 2 mM Ca. These substitutions reduced the sodium current that would otherwise have contaminated the calcium current record, and increased the calcium current above what it would have been with only 2 mM Ca in the bath. Potassium currents were blocked by tetraethylammonium (TEA) in the bath and cesium (Cs) in the pipet solution.

As seen from FIG. 3, curve A, the calcium current activates quickly (within about 20 ms) and inactivates with a time constant of 30 to 40 ms. The calcium current is measured by the amplitude of the peak inward current elicited by the depolarization peak, and has a measured value of about −1200 pA. The cell in FIG. 3 (curve A) was also exposed to 1 μM nifedipine, a dihydropyridine, which is expected to effectively block L-type calcium channels in the neuroblastoma cells, and no effect on the measured calcium current was observed. The calcium current observed is thus not dihydropyridine-sensitive.

Figure 4:
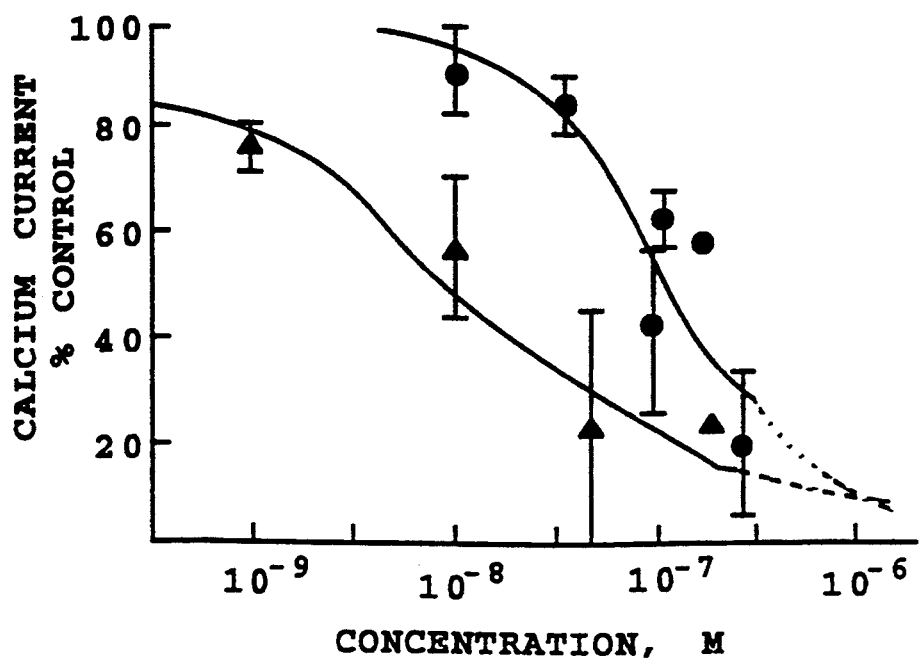
FIG. 4 plots the percent inhibition of peak inward calcium currents in neuroblastoma cells as a function of OCT MVIIA (SNX-111) (solid triangles) and OCT GVIA (SNX-124)(solid circles)

The responses of voltage-gated calcium currents to increasing concentrations of OCTs MVIIA (SNX-111) and GVIA (SNX-124) are shown in FIG. 4. The $IC_{50}$ concentration, at which 50% inhibition of calcium current is produced, is determined from the voltage-gated current amplitudes, plotted as a function of omega-conopeptide concentration. The calculated $IC_{50}$ is about 10 nM for GVIA and 100 nM for MVIIA, indicative of high inhibitory peptide activity. The $IC_{50}$ concentration for these and omega-conopeptides SVIA (SNX-157) and SVIB (SNX-183) are given in Table 1 below.

TABLE 1

| Inhibition of calcium currents in N1E-115 neuroblastoma cells | |
|---|---|
| Compound | $IC_{50}$ |
| GVIA (SNX-124) | 10 nM |
| MVIIA (SNX-111) | 100 nM |
| SVIB (SNX-183) | >1 μM |
| SVIA (SNX-157) | >20 μM |

Calcium currents were also measured in human neuroblastoma IMR32 cells, using techniques described above and in Example 1. Voltage-gated calcium currents were elicited by holding the cell(s) at −70 mV and administering a step-voltage to −10 mV. Current tracings from IMR-32 cells bathed in control medium (lower curve) and in medium containing 150 nM SNX-111 (upper curve) are shown in FIG. 5A. The amplitude of the current is shown on the abscissa. The peak inward current is shown as the difference between the resting potential shown at the far left side of the figure and the lowest point of the curve, just adjacent to the resting value. In this experiment, attenuation of voltage-gated calcium current is apparent in the presence of SNX-111 (upper curve), as shown by the decreased amplitude of the peak inward current.

Figure 5C:
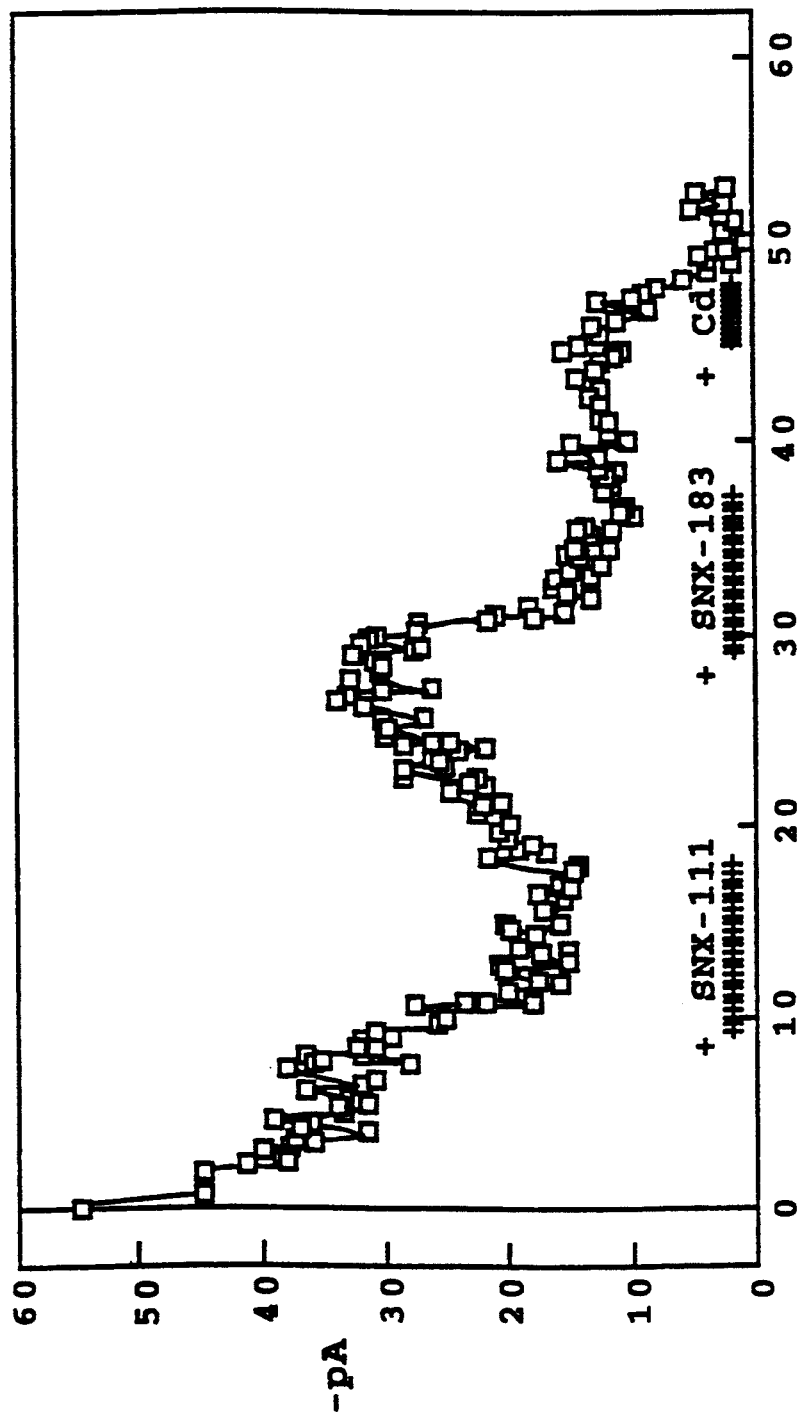

FIGS. 5B and 5C show cumulative data from many consecutive currents, elicited at 15 second intervals as described above, in IMR-32 cells. In these plots, peak inward current recorded from each stimulus is recorded sequentially as a single data point. In the experiment illustrated in FIG. 5B, addition of SNX-111 to the bathing medium resulted in decreased peak inward currents; restoration of substantially normal calcium currents was achieved after washing of the compound from the cell chamber, shown on the right side of the figure. FIG. 5C shows the effects of 150 nM SNX-111 and SNX-183 added sequentially to a single cell preparation. Both compounds resulted in attenuation of peak inward current; though recovery following SNX-183 exposure was not observed. Addition of cadmium (Cd) to the medium resulted in blockade of all remaining voltage-gated calcium currents in this preparation.

Test peptides which are inhibitory for neuronal cell calcium currents can be further tested in non-neuronal cells, to confirm that the peptide activity in blocking calcium currents is specific to neuronal cells. A variety of muscle cell types which are refractory to calcium-current inhibition by OCTs, such as vertebrate embryo heart and skeletal muscle cells, are suitable. Cell current measurements are made substantially as outlined above and detailed in Example 1. OCT MVIIA, for example, has been reported to block voltage-gated calcium channels in a variety of neuronal cells, including dorsal root ganglion (DRG) neurons (McCleskey). This blockage or inhibition of calcium channel currents has been reported to be neuron-specific, since calcium current inhibition by the peptide was not observed in cardiac, smooth, and skeletal muscles.

2. Specific, High Affinity Binding to OCT Receptors

Omega-conopeptides have been shown, in accordance with the invention, to bind with high affinity to specific binding site(s) in neuronal cells. In accordance with the selectivity of the compound, the binding affinity can be characterized either by the binding constant of the compound for the MVIIA (SNX-111) binding site, also referred to as "site 1" herein, or the binding constant of the compound for the SVIB (SNX-183) or the MVIIC (SNX- 230/SNX-231) binding site, also referred to as "site 2" herein. Evidence for the existence of at least two distinct OCT binding sites is summarized below. In some cases, when specific binding to one site is preferred, it will be useful to characterize omega-conopeptides according to the ratio of their binding constants measured for binding to neuronal-cell MVIIA (SNX-111) binding site 1 and SVIB (SNX-183) binding site 2.

Binding to the OCT MVIIA binding site in neuronal tissue can be demonstrated with a variety of cell types and synaptosomal cell fractions. One preferred neuronal membrane is a mammalian brain synaptosomal preparation, such as the rat brain synaptosome preparation described in Example 2. The binding constant of a compound for the MVIIA binding site is typically determined by competitive displacement of radiolabeled OCT MVIIA (SNX-111) from the synaptosomal preparation, as follows.

Figure 6A:
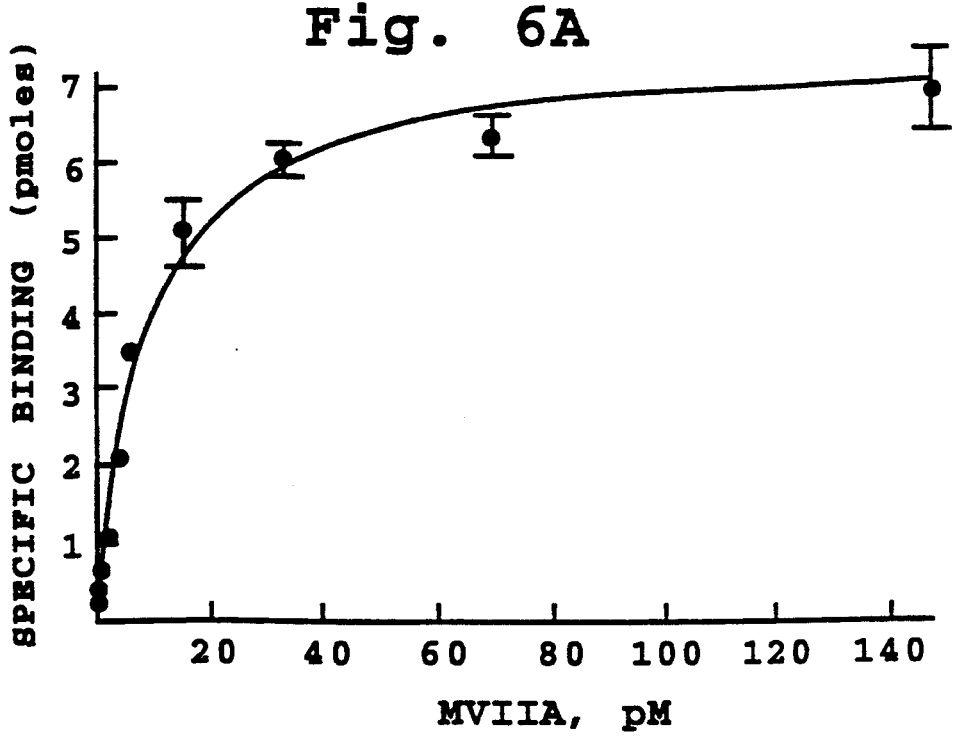
FIGS. 6A and 6B are a binding curve showing the amount of radioiodinated OCT MVIIA (SNX-111) bound to rat synaptosomal membranes, as a function of OCT MVIIA (SNX-111) concentration (6A), and the same data plotted as a Scatchard plot (6B)

The binding constant $K_d$ of the MVIIA (SNX-111) peptide for the synaptosomal membranes is determined by a saturation binding method in which increasing quantities of radiolabeled peptide are added to the synaptosomal membranes, and the amount of labeled material bound at each concentration is determined (Example 3A). The plot of bound peptide as a function of concentration is then used to calculate a $B_{max}$, the concentration of binding sites on the synaptosomes, and $K_d$ following standard methods. In particular, the $K_d$ value is the calculated concentration of peptide needed to half saturate the synaptosomal specific binding sites. FIG. 6A shows the specific binding of radiolabeled OCT MVIIA (SNX-111) to rat brain synaptosomes, plotted as a function of omega-conopeptide concentration, and FIG. 6B, the same data in Scatchard plot form. From the slope of the Scatchard plot line, a $K_d$ binding value of 10 pM is obtained. Similarly, $K_d$'s were determined for binding of radiolabelled SVIB (SNX-183) to binding sites in synaptosomal membranes.

Reversibility of binding is a characteristic of ligands which, under equilibrium conditions, freely associate with and dissociate from their respective binding sites. Reversibility of binding of a specific compound is demonstrated by the labelled compound's ability to be displaced by unlabelled compound, after equilibrium binding of the labelled compound has been achieved. That is, in the binding experiments described in Example 3B, a synaptosomal preparation is incubated with labelled compound for a time period sufficient to produce a stable level of binding, then excess unlabelled compound is added to the preparation, and the preparation is assayed for bound labelled compounds at various time points thereafter.

Figure 7:
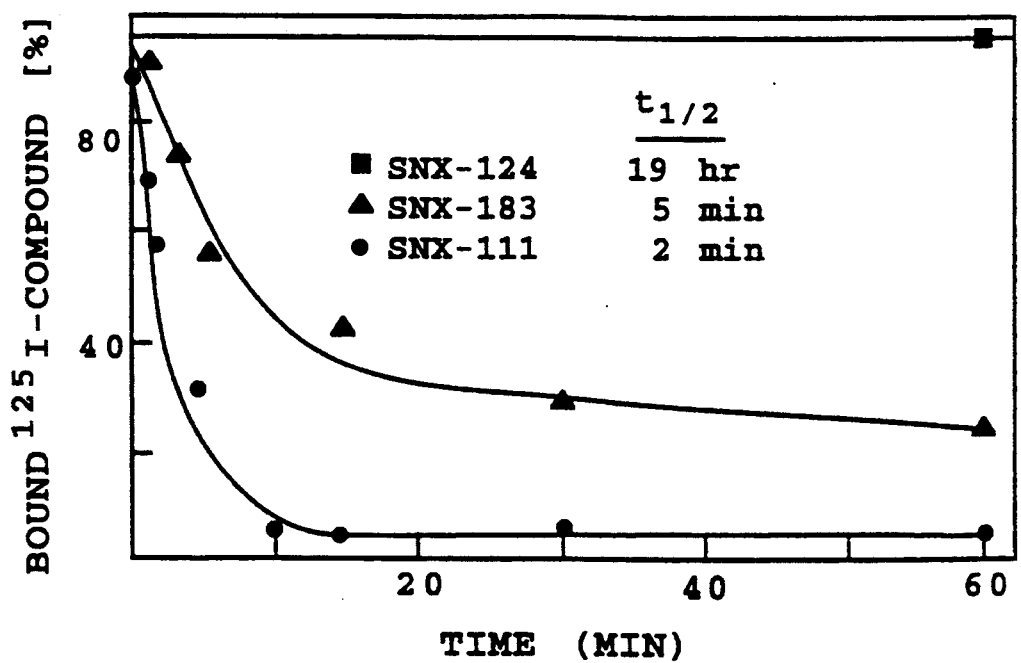
FIG. 7 shows reversibility of equilibrium binding of radioiodinated SNX-111 and SNX-183, and irreversibility of binding of radioiodinated SNX-124 to rat brain synaptosomal membranes.

If the labelled compound binds reversibly to the preparation, a reduction of labelled binding, to essentially non-specific binding levels, will be observed over time. FIG. 7 shows a plot of the dissociation kinetics of labelled SNX-111, SNX-183 and SNX-124. In contrast to SNX-111 binding, OCT GVIA (SNX-124) binds irreversibly to synaptosomal membranes. SNX-124 binding can therefore be said to be essentially irreversible, while SNX-111 and SNX-183 bind reversibly to their respective binding sites.

Figure 8A:
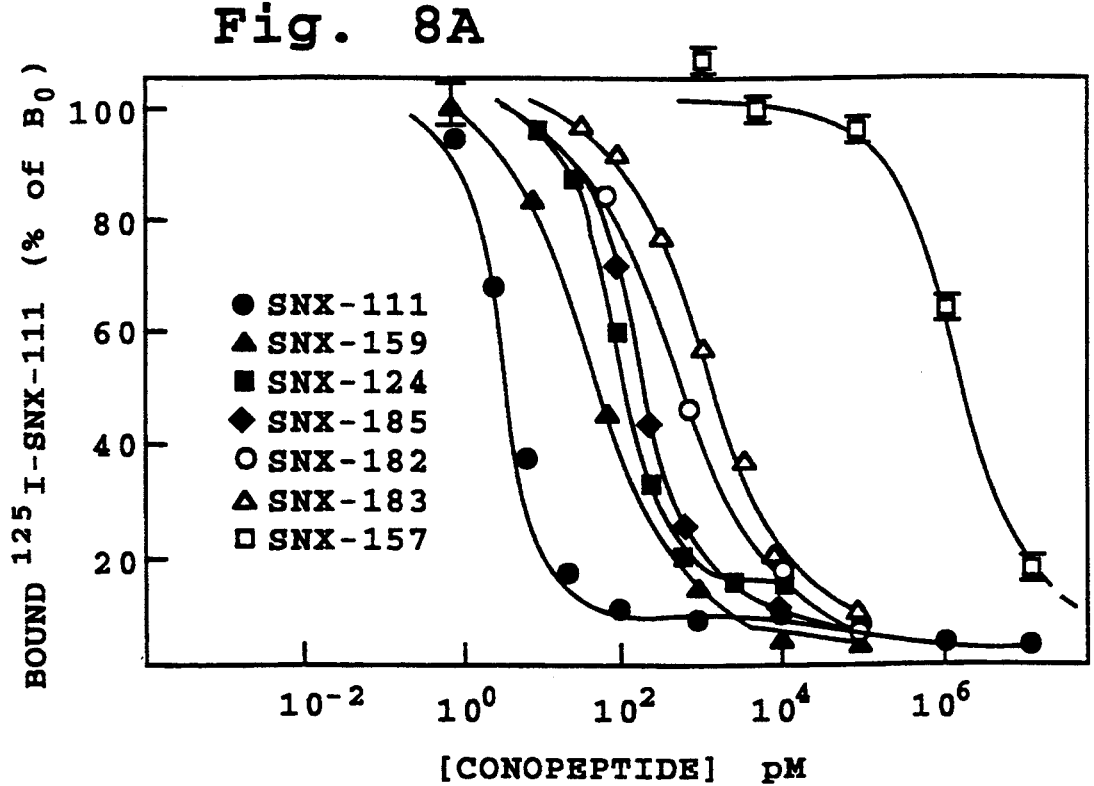
FIGS. 8A and 8B show computer-fit competitive binding curves for omega-conopeptide binding to the OCT MVIIA (SNX-111) binding site in rat brain synaptosomes.
Figure 8B:
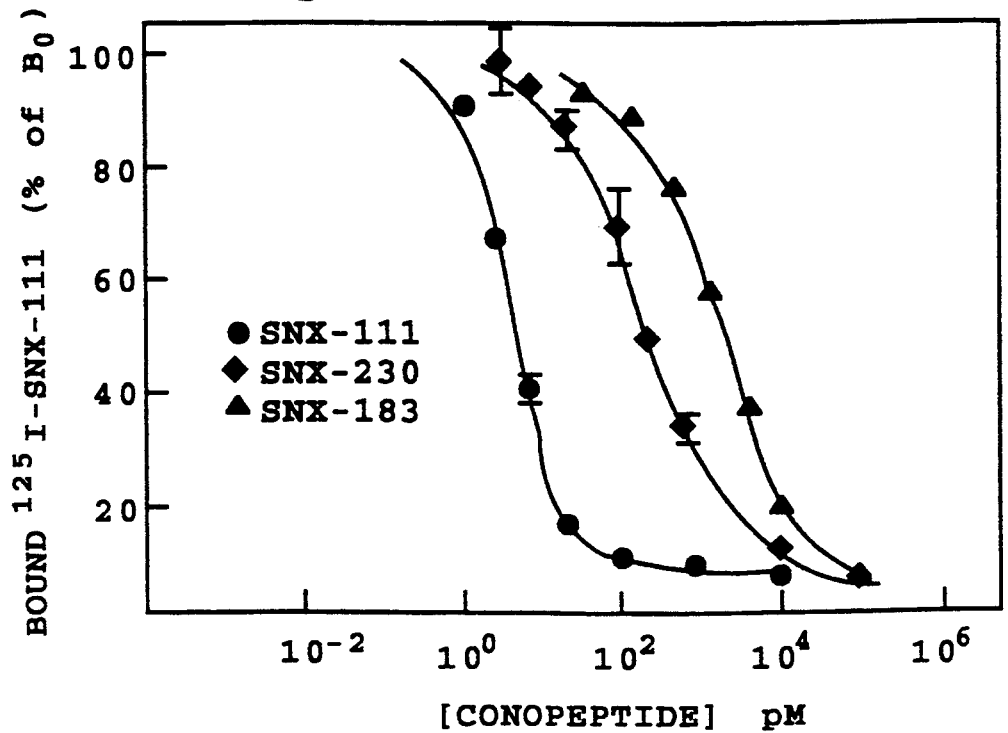

To determine the binding constant of a test compound for an OCT binding site, the test compound is added, at increasing concentrations, to the synaptosome preparation in the presence of a standard concentration of radiolabeled OCT, such as OCT MVIIA (SNX-111). The synaptosomal material is then rapidly filtered, washed and assayed for bound radiolabel. The binding constant ($K_i$) of the test compound is determined from computer-fit competitive binding curves, such as shown in FIGS. 8A and 8B for MVIIA (SNX-111) peptide, to determine first the $IC_{50}$ value of the compound, i.e., the concentration which gives 50% displacement of labeled MVIIA peptide, then calculating $K_i$ from the $K_d$ value of OCT MVIIA and the $IC_{50}$ value of the compound, as detailed in Example 3. A relative potency value can also be calculated from this information (Example 3). Like the $K_i$ value, this value allows comparisons between assays performed at different times. Calculated $IC_{50}$ values for a number of omega-conopeptides for binding of OCT MVIIA (SNX-111) are given in Table 2. The compounds are arranged in order of increasing $IC_{50}$ values.

TABLE 2

| Competition of $^{125}$I-MVIIA (SNX-111) Binding of OCT Peptides | | |
|---|---|---|
| | | $IC_{50}$ (nM) |
| | SNX-207 | .007 |
| | SNX-194 | .008 |
| | SNX-195 | .009 |
| MVIIA | (SNX-111) | .013 |
| | SNX-190 | .021 |
| | SNX-200 | .039 |
| | SNX-201 | .046 |
| | SNX-202 | .046 |
| | SNX-193 | .070 |
| | SNX-231 | .153 |
| MVIIC | (SNX-230) | .320 |
| MVIIB | (SNX-159) | .101 |
| GVIA | (SNX-124) | .134 |
| | SNX-198 | .160 |
| | SNX-191 | .165 |

TABLE 2-continued

| Competition of $^{125}$I-MVIIA (SNX-111) Binding of OCT Peptides | | |
|---|---|---|
| | | $IC_{50}$ (nM) |
| TVIA | (SNX-185) | .228 |
| | SNX-196 | .426 |
| RVIA | (SNX-182) | .893 |
| SVIB | (SNX-183) | 1.5 |
| GVIIA | (SNX-178) | 3.70 |
| | SNX-197 | 11.3 |
| SVIA | (SNX-157) | 1460. |

Figure 9A:
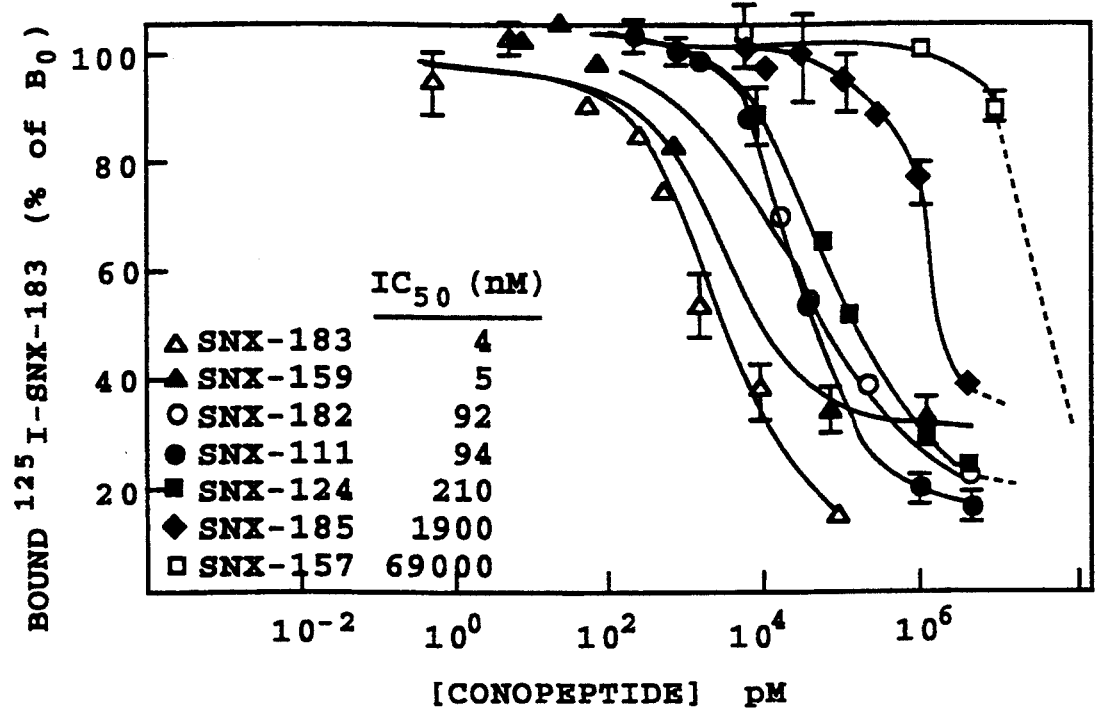
FIG. 9A shows computer-fit competitive binding curves for omega-conopeptide binding to the OCT SVIB (SNX-183) binding site in rat brain synaptosomes.
Figure 9B:
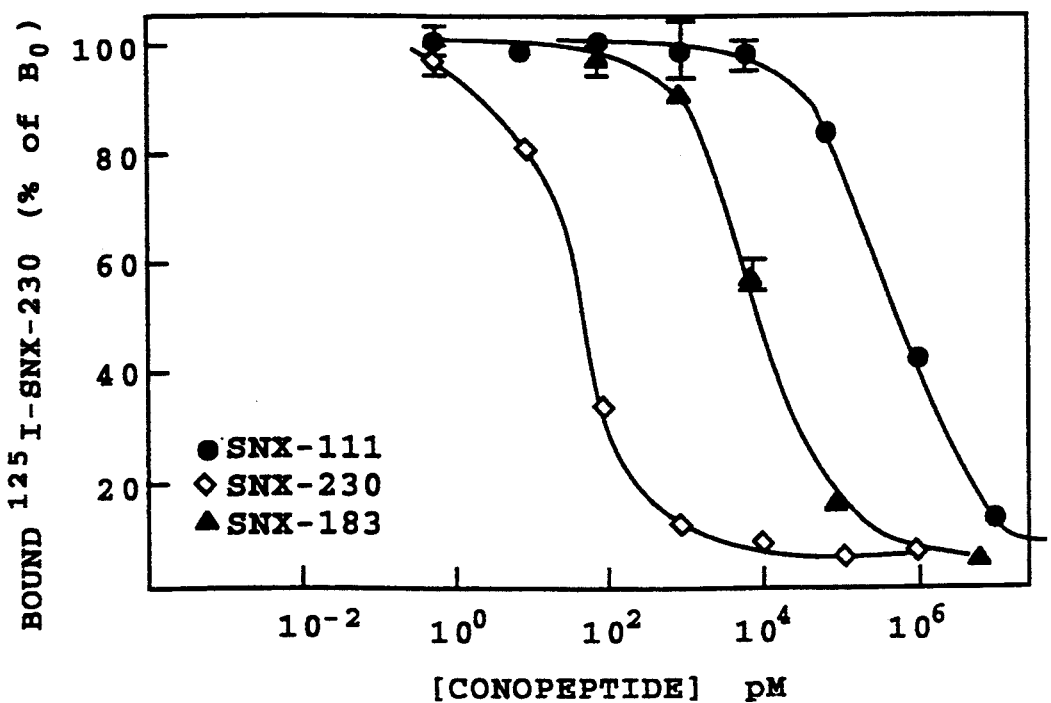
FIG. 9B shows binding site competitive binding curves for the binding of OCT MVIIC (SNX-230)

Similarly, $IC_{50}$ and $K_i$ values for compound binding to the SVIB (SNX-183) binding site can be calculated, as above, by determining the $K_d$ of labeled OCT SVIB (SNX-183) or OCT MVIIC (SNX-230) binding to a synaptosome preparation, then using competitive displacement of the labeled compound by the test compound, to determine the $IC_{50}$ and $K_i$ or relative potency values of the test compound. FIGS. 9A and 9B show computer-fit competitive binding curves for several omega-conopeptides whose binding to the SVIB (SNX-183) and MVIIC (SNX-230) binding site (site 2) was examined. From these curves, $IC_{50}$ values were determined as above.

Table 3 lists the relative potencies for binding of various omega-conopeptides to the MVIIA and SVIB binding sites, and shows the ratio of such relative potency values for binding of each compound to the sites, defined by bending of [$^{125}$I]MVIIA and [$^{125}$I]SVIB, respectively. Compounds SNX-230 and SNX-231, which differ by a single hydroxyl group (hydroxyl vs. hydroxylproline at position 7, FIG. 1), gave very similar binding profiles.

TABLE 3

| Relative Potencies of Omega-conopeptides at OCT Binding Sites | | | |
|---|---|---|---|
| | Relative Potency | | Ratio |
| | MVIIA Site | SVIB Site | MVIIA/ SVIB |
| MVIIA (SNX-111) | 1 | .022 | 45. |
| GVIA (SNX-124) | .072 | .014 | 5 |
| TVIA (SNX-185) | .04 | .00094 | 46 |
| SNX-207 | 1.5 | .0019 | 789. |
| SNX-218 | .054 | .019 | 2.8 |
| SNX-201 | .25 | .49 | 0.5 |
| SNX-202 | .24 | .33 | 0.7 |
| SVIB (SNX-183) | .012 | 1.0 | 0.01 |
| SVIA (SNX-157) | $7 \times 10^{-7}$ | $4.1 \times 10^{-5}$ | 0.02 |
| MVIIC (SNX-230) | .021 | 287 | $7.32 \times 10^{-5}$ |
| SNX-231 | .044 | 230 | $1.9 \times 10^{-4}$ |

The identity of the MVIIA and SVIB binding sites in neuronal-cell synaptosomal membranes was examined by binding radiolabeled OCT MVIIA to synaptosomes, and crosslinking the peptide to the neuronal membranes, as detailed in Example 4. The labeled membranes were solubilized with sodium dodecyl sulfate (SDS), fractionated by polyacrylamide gel electrophoresis (PAGE), and examined by autoradiography for labeled polypeptide bands. In one case, the membranes were incubated with labeled peptide in the presence of excess unlabeled OCT MVIIA. A similar binding study was carried out with labeled OCT SVIB.

Evidence that the two receptor sites identified by SNX-111 and SNX-183 are distinct was obtained from affinity crosslinking studies in which [$^{125}$I]-SNX-111 and [$^{125}$I]-SNX-183 were chemically crosslinked to rat brain synaptosomal membrane preparations and then subjected to SDS-PAGE followed by autoradiography (FIG. 10). IC$_{50}$ for site 1 determined by binding assays (FIG. 8). Labeling of this 210 kDa band by [$^{125}$I]-SNX-111 was also inhibited by SNX-183 but with lower affinity (IC$_{50}$ 300 pM). Similar experiments with [$^{125}$I]-SNX-183 revealed that in addition to the expected labeled band at 210 KDa, three additional bands at 172, 150 and 138 kDa appear to be specifically labeled (FIG. 10B).

Analysis of the inhibition of incorporation of [$^{125}$I]-SNX-183 in the 210 kDa band by SNX-111 provides evidence for the presence of two distinct polypeptides of M$_r$ 210 kDa corresponding to site 1 and site 2 (FIG. 11). SNX-111 displaced [$^{125}$I]-SNX-183 from the 210 kDa polypeptide in a biphasic manner with IC$_{50}$ values of 6 pM and 65 nM. At low concentrations, SNX-111 effectively competed against [$^{125}$I]-SNX-183 for binding to site 1, while the binding of [$^{125}$I]-SNX-183 to site 2 was competitively displaced by SNX-111 only at much higher concentrations.

Figure 11A:
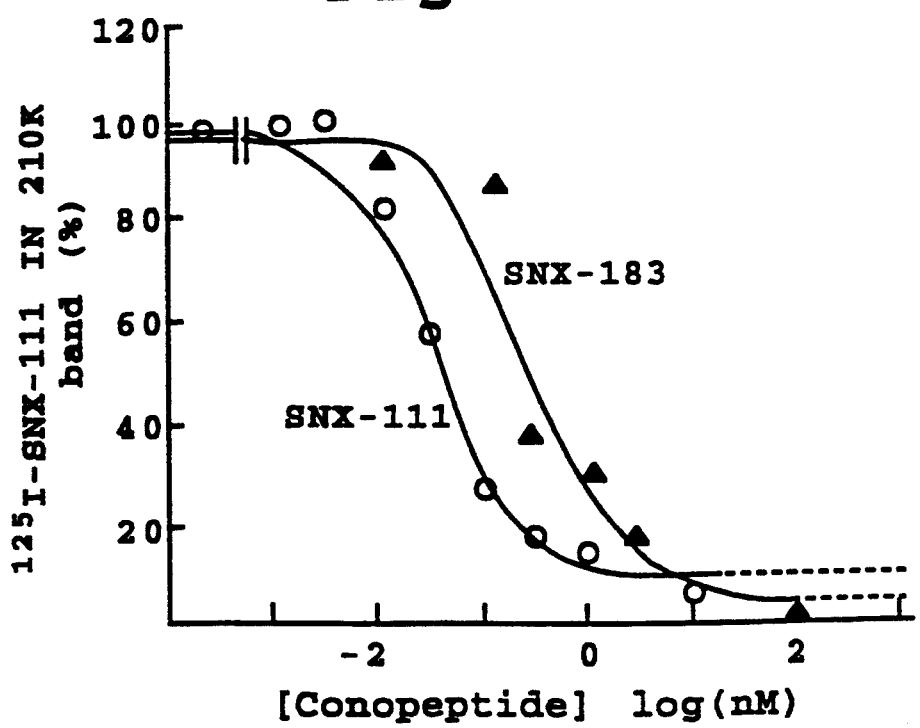
FIGS. 11A and 11B shows plots of competition by unlabeled SNX-111 and SNX-183 for binding of [$^{125}$I]-SNX-111 (11A) and [$^{125}$I]-SNX-183 (11B) to the 210 kilodalton band of polypeptides present in rat synaptosomal membranes.

Inhibition of incorporation of [$^{125}$I]-SNX-183 into the 210 kDa band by SNX-183 is consistent with the ability of this compound to bind to both site 1 and site 2, but, as shown above, with much lower affinity than MVIIA (SNX-111) or TVIA (SNX-185) at site 1. The displacement of MVIIA binding by SNX-183 is characteristically shallow, with an IC$_{50}$ of 360 pM (FIG. 11A). Taken together with the differential rank orders of binding affinities for omega-conopeptides at the two binding sites, as measured by displacement, these cross-linking experiments strongly suggest that the conopeptide binding components of site 1 and site 2 are distinct molecular entities both with M$_r$ 210 kDa.

3. Localization of Binding of Omega-conopeptides in Nervous Tissue

The omega-conopeptide binding sites described above are distributed differentially throughout the nervous system. The regional distribution of the binding sites and their relative affinities for the two conopeptides SNX-111 and SNX-183 in rat brain sections were determined by autoradiography of brain sections exposed to the radiolabeled compounds, detailed in Example 5. The results presented in FIG. 12 show that the distribution of binding of [$^{125}$I]-SNX-111 is highly localized (A, B) and that non-specific binding is virtually non-existent (C, D). The pattern of binding is similar to that reported using [$^{125}$I]-GVIA preparations (Takemura). Comparison of the specific binding of [$^{125}$I]-SNX-111 and [$^{125}$I]-SNX-183 revealed overlapping but differential distribution of binding sites (E, F). Both ligands labeled the cortex, CA1, dentate gyrus and caudate-putamen. In these regions, binding of [$^{125}$I]-SNX-183 was unaffected by concentrations of SNX-111 which caused complete displacement of [$^{125}$I]-SNX-111 labeling (not shown), suggesting colocalization of sites 1 and 2. Greater abundance of site 2 in thalamic ventromedial lateral lobe and medial geniculate was revealed by the high density of binding of [$^{125}$I]-SNX-183 in these nuclei. In contrast, globus pallidus, CA3 and substantia nigra were labeled only by [$^{125}$I]-SNX-111, indicating a preponderance of site 1 in these regions. Computer-aided densitometric analysis of the displacement of [$^{125}$I]-SNX-111 by SNX-183 in the different regions showed that the labeling of cortex and hippocampus by [$^{125}$I]-SNX-111 could be inhibited by lower concentrations of SNX-183 (IC$_{50}$ 100 nM) whereas higher concentrations of SNX-183 (IC$_{50}$ 300 nM) were needed to displace [$^{125}$I]-SNX-111 from the substantia nigra. The complete absence of [$^{125}$I]-SNX-183 binding in the substantia nigra suggests a third, distinct binding site recognized only by [$^{125}$I]-SNX-111, and by implication, a novel calcium channel subtype.

Since a number of nuclei that are known to be rich in synapses and thus likely to contain a high density of presynaptic calcium channels were not labeled by either ligand, the two conopeptides can distinguish four different subtypes of neuronal binding sites, as summarized in Table 4. The four subtypes are: those sensitive to both SNX-111 and SNX-183 (site 1), those sensitive to SNX-183 only, (site 2), those recognized by SNX-111, only and others recognized by neither conopeptide.

TABLE 4

Four classes of OCT binding site calcium channels

| Site | Binds SNX-111 | Binds SNX-183 | Examples |
|---|---|---|---|
| 1 | + | + | cortex, hippocampal CA1, CA3, thalamic nuclei, spinal cord (laminae I + II only) |
| 2 | – | + | cortex, hippocampal CA1, CA3, thalamic nuclei, spinal cord |
| 3 | – | – | midbrain nuclei, spinal grey matter (except laminae I + II), neuromuscular junction |
| 4 | + | – | substantia nigra, hippocampal CA2 |

4. Selective Inhibition of Neurotransmitter Release

Omega-conopeptides inhibit neurotransmitter release in various regions of the nervous system. As shown below, such inhibition varies according to the neurotransmitter, the omega-conopeptide, and the region studied. Neurotransmitters which can be measured, in accordance with various aspects of the invention, include, but are not limited to dopamine, norepinephrine, acetylcholine, GABA, glutamate, and a number of peptide neurotransmitters, such as substance P (McGeer).

Quantitation of release and inhibition thereof is determined by sensitive detection methods, also known in the art, including direct detection of release of endogenous stores by HPLC or specific radioimmunoassay (RIA), and detection of release of pre-loaded, labeled compound. Alternatively, or in addition, detection of release may be achieved using a number of indirect assays, exemplified above, in which whole tissue response to electrical or chemical stimulation is measured.

Inhibition of release of the neurotransmitter norepinephrine from neuronal cells can be assayed in mammalian brain hippocampal slices by standard methods, such as detailed in Example 6A. Briefly, hippocampal slices are distributed to individual wells of a microtiter plate, and incubated with radiolabeled norepinephrine under conditions favoring cell uptake. The cells are washed with a low-potassium medium, then bathed for 15 minutes in a high-potassium stimulation medium, in the presence of selected concentrations of the test compound. After removal of the stimulation buffer, radioactivity remaining in each slice is determined.

Figure 13A:
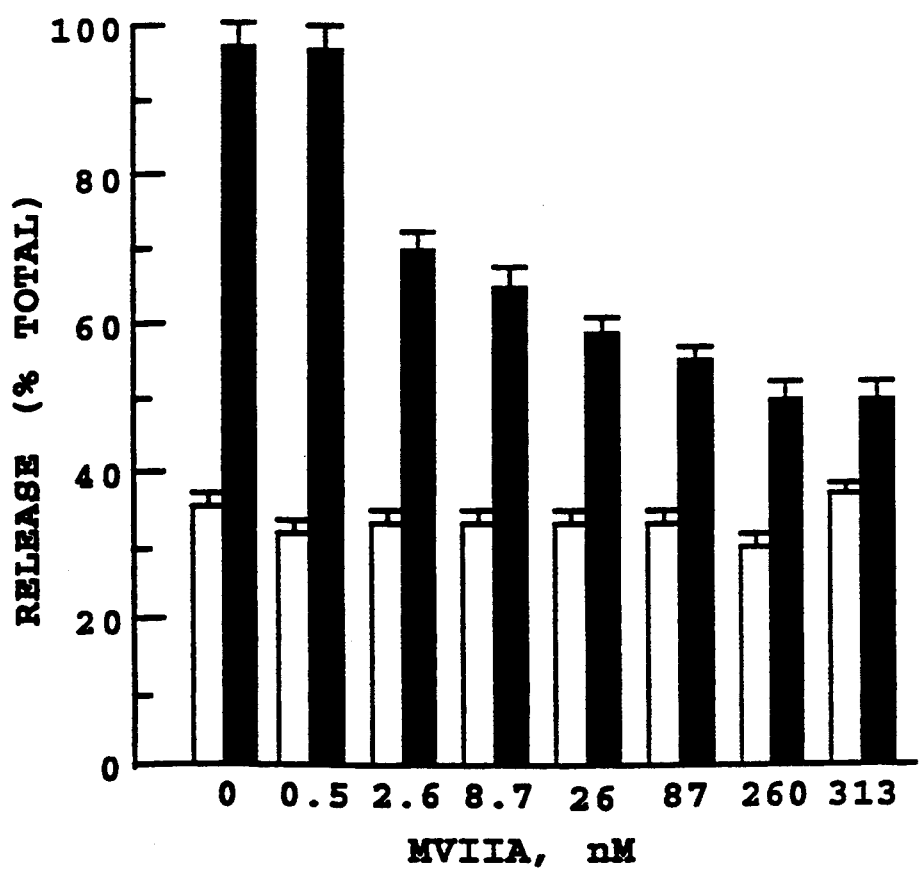
FIG. 13A shows the inhibition of [$^3$H]norepinephrine release from rat hippocampal slices as a function of OCT MVIIA (SNX-111) concentration (solid bars are potassium stimulated and open bars are basal values)

FIG. 13A shows concentration dependence of inhibition of norepinephrine release from hippocampal slices, as detailed in Example 6A. Basal (open bars) and potassium-stimulated (solid bars) release in shown in the presence of varying concentrations of SNX-111, as indicated.

Figure 13B:
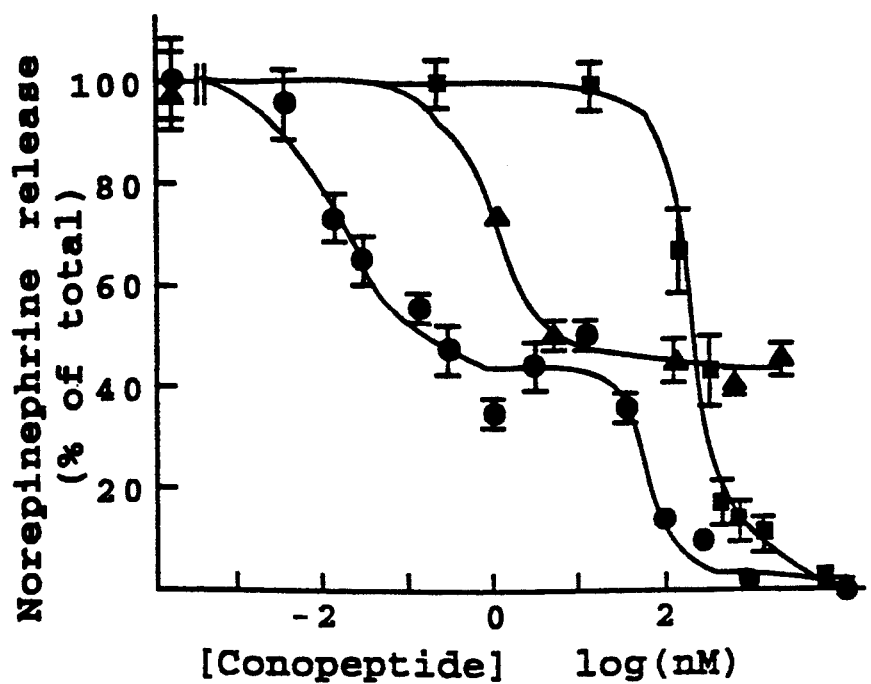
FIG. 13B shows the dose-dependent inhibition of potassium-stimulated release of [$^3$H]norepinephrine by OCT MVIIA (SNX-111; triangles), and OCT SVIB (SNX-183; squares), and OCT MVIIC (SNX-230; circles)

FIG. 13B shows the effects of the three peptides SNX-111, SNX-183 and SNX-230 on the release of norepinephrine evoked by potassium depolarization. SNX-111 inhibits release with high potency (IC$_{50}$ ≈ 1 nM) but only partially (approx. 60%). SNX-183 is much less potent (IC$_{50}$ ≈ 180 nM) but the inhibition is substantially 100%. SNX-230 also inhibits release 100%, but in a biphasic manner, inhibiting approximately 50% with high potency (IC$_{50}$=0.02 nM) and 50% with much lower potency (IC$_{50}$ =65 nM). In agreement with the binding studies discussed above, these results imply that such norepinephrine release is mediated by at least two distinct subtypes of presynaptic calcium channels, one of which corresponds to the site 1 receptor identified by high affinity for SNX-111 and the other to the site 2 receptor recognized preferentially by SNX-230.

The IC$_{50}$ values given in Table 5 for a variety of omega-conopeptides which have been examined by this method represent the average IC$_{50}$ values calculated from thin (200µ and thick (400µ) hippocampal slices. The three lowest IC$_{50}$ values, between 0.8 and 2.4 nM, correspond to omega-conopeptides which are most potent in this assay.

TABLE 5

Inhibition of Norepinephrine Release by Omega-conopeptides

| omega-conopeptides | IC$_{50}$ (nM) |
| --- | --- |
| GVIA (SNX-124) | 0.8 |
| MVIIA (SNX-111) | 1.5 |
| TVIA (SNX-185) | 2.4 |
| SNX-201 | 11 |
| SNX-195 | 11 |
| MVIIC (SNX-230) (at site 1) | 65 |
| SNX-202 | 29 |
| SVIB (SNX-183) | 200 |
| SNX-191 | >100 |
| SVIA (SNX-157) | >4500 |

The selective effect of omega-conopeptides in inhibiting neurotransmitter release from specific types of nerve terminals is demonstrated by the markedly different responses of other neurotransmitter systems, when exposed to omega-conopeptides. When tested in a synaptosomal preparation prepared from the neuronal rich electric organ of electric eel (*Ommata dyscopyge*), a different rank order of potency was observed (Table 6).

TABLE 6

Inhibition of Release of ATP from Electric Organ Synaptosomes

| Compound | IC$_{50}$ |
| --- | --- |
| SNX-111 | 42 |
| SNX-195 | 84 |
| SNX-183 | 1,700 |
| SNX-185 | >6,000 |
| SNX-157 | >6,000 |

Similarly, inhibition of release of amino acid neurotransmitters GABA and glutamate from rat neuronal tissue did not parallel either binding potency at the MVIIA site 1, the SVIB site 2 or inhibition of norepinephrine release (Table 7).

TABLE 7

Inhibition of release of GABA and Glutamate from rat Synaptosomes

| Compound | IC$_{50}$ (GABA) | IC$_{50}$ (Glutamate) |
| --- | --- | --- |
| SNX-185 | 100 nM | >100 nM |
| SNX-183 | 200 nM | 200 nM |

TABLE 7-continued

Inhibition of release of GABA and Glutamate from rat Synaptosomes

| Compound | IC$_{50}$ (GABA) | IC$_{50}$ (Glutamate) |
| --- | --- | --- |
| SNX-111 | >200 nM | >200 nM |

Effects of omega-conopeptides were also compared to those of OCT GVIA and amiodipine, an L-channel blocker, on potassium-stimulated release of dopamine and acetylcholine from slices of rat brain (striatal region) as described in Example 6 (C,D). Briefly, in these experiments, striatal slices from rat brain were preloaded with radiolabelled dopamine or choline, then perfused for 45 minutes with bathing media. Slices were subjected to an S1 stimulus, consisting of addition of 15 mM potassium chloride to the bathing medium for 1 minute. Total outflow of radiolabeled neurotransmitter in response to S1 was measured. Slices were then washed, exposed to test compound for 20 minutes, then subjected to an S2 stimulus, as above. Comparison of outflow of neurotransmitter in response to S2 to outflow in response to S1 is a measure of drug effects on the system. Results are given as percent inhibition of release in Tables 8 and 9.

TABLE 8

Effect of Omega-conopeptides and amiodipine on [$^3$H] dopamine release from striatal slices

| Compound | Concentration | % inhibition |
| --- | --- | --- |
| GVIA | 1 nM | 5 |
|  | 10 nM | 52 |
| MVIIA | 1 nM | 6 |
|  | 10 nM | 49 |
| Amiodipine | 1000 nM | 0 |

TABLE 9

Effect of Omega-conopeptides and amiodipine on [$^3$H] acetylcholine release from striatal slices

| Compound | Concentration | % inhibition |
| --- | --- | --- |
| GVIA | 3 nM | 50 |
| MVIIA | 5.5 nM | 50 |
| Amiodipine | 1000 nM | 0 |

Further means of measuring inhibition of neuronal transmitter release are isolated tissue assays, such as atrial strip, aorta, vas deferens and guinea pig ileum assays, in which the response to a stimulus, usually an electrical stimulus, is correlated to the amount of neurotransmitter released from neurons innervating the tissue (Kenakin). In the guinea pig ileum, inhibition of electrically stimulated contractions is correlated with inhibition of acetylcholine release, as demonstrated by the ability of cholinergic agonists to overcome such inhibition. Example 6E describes the preparation and assay in detail. Table 10 shows the IC$_{50}$ values for various omega-conopeptides on contraction of guinea pig ileum in response to electrical stimulation.

TABLE 10

Effects of Conopeptides on electrically stimulated contraction of Guinea pig ileum

| Compound | IC$_{50}$ (nM) |
| --- | --- |
| SNX-111 | 10 |
| SNX-185 | 30 |
| SNX-183 | 90 |
| SNX-157 | >100 |
| SNX-230 | 200 |

II. Treatment of Pain

In accordance with one aspect of the invention, it has been discovered that omega-conopeptides TVIA (SNX-185) or MVIIA (SNX-111), or derivatives thereof which are effective (a) to inhibit voltage-gated calcium channels selectively in neuronal tissue, as evidenced by the peptide's ability to inhibit electrically stimulated contraction of the guinea pig ileum, and (b) to bind to omega-conopeptide MVIIA binding sites present in neuronal tissue, are effective to produce analgesia and to enhance the analgesic effect of an opiate compound.

A. Omega-conopeptides

Omega-conopeptides useful in the treatment of pain have been found, in accordance with the invention, to conform to certain physical and chemical constraints, as described below. Generally, omega-conopeptides useful in the treatment methods are those which are 25-35 amino acids in length and which have three disulfide bonds at specified positions along their length.

Based on a sequence homology analysis of the peptides whose full sequences are known (FIG. 1), the naturally occurring active omega-conopeptides were grouped into distinct groups I and II, each with internal homologies distinct to that group, as can be appreciated from FIG. 14. Group I includes active omega-conopeptides MVIIA (SNX-111) and MVIIB (SNX-159) which possesses a binding constant to the MVIIA site within the range of compounds showing activity in treating pain. Group II includes active omega-conopeptides TVIA (SNX-185) and SNX-207. A third group includes inactive peptides SNX-231, and SVIA (SNX-157) and omega-conopeptides whose binding activities for the MVIIA site on neuronal membranes and/or activity in norepinephrine inhibition are outside the range of active compounds.

The three groups of omega-conopeptides are arranged in FIG. 14 with their six Cys residues aligned, which places these residues at positions 1, 8, 15, 16, 20, and 28. To make this alignment, gaps were introduced at the positions shown in the three groups. In the analysis below, these gaps retain the assigned number shown in FIG. 14, even though they represent amino acid deletions in the respective groups of active omega-conopeptides.

Sequence variation in the peptides, based on primary structure alone, was analyzed by adopting the following constraints:

1. The peptides in both active groups (I and II) include the Cys residues at position 1, 8, 15, 16, 20, and 28. Other Cys residues could be substituted at the positions indicated below only if they are selectively protected during oxidation of the peptide to form the three disulfide linkages.

2. The peptides in the active groups include three disulfide linkages connecting the Cys residues at positions 1 and 16, 8 and 20, and 15 and 28. As described above, the disulfide bridges are formed by air oxidation of the full sequence peptide in the presence of DTT. The ability of the peptide to form the three desired disulfide linkages would therefore require that the peptide, prior to disulfide bridging, be able to adopt a conformation which allows the three selected linkages, with or without the Cys protecting-group strategy discussed above. This constraint would thus exclude amino acid variations which prevent or otherwise hinder the formation of the three selected bridges.

Constraints 1 and 2 preserve the basic conformation of the omega-conopeptides imposed by the three disulfide bridges.

3. Within Group I, the amino acid variations which occur at the six non-conserved residues are allowed, including peptides in which the carboxy terminus is amidated or has a free acid form. That is, the first group compound derivatives include the peptide structures having the form: SEQ ID NO: 22-$X_1$-SEQ ID NO: 23-$X_2$-SEQ ID NO: 25-$X_3X_4$-SEQ ID NO: 24-$X_5$-SEQ ID NO: 25-$X_6$-SEQ ID NO: 26-t, where $X_1$=K or S; $X_2$=S or H; $X_3$=L or T; $X_4$=M or S; $X_5$=N or a deletion; $X_6$=S or deletion, and t=a carboxy or amidated carboxyterminal group, and where SEQ ID NO: 22 is C K G K G A; SEQ ID NO: 23 is C; SEQ ID NO: 25 is R; SEQ ID NO: 24 is Y D C C T G S C; and SEQ ID NO: 26 is G K C.

4. Within Group II, the amino acid variations which occur at the eight non-conserved residues are allowed, including peptides in which the carboxy terminus is amidated or has a free acid form. Thus, the second group compound derivatives include the peptide structures having the form: SEQ ID NO: 27-$X_1X_2X_3$-SEQ ID NO: 28-t, where $X_1$=X or R; $X_2$=T or L; $X_3$=S or M, and t=a carboxy or amidated carboxyterminal group, and where SEQ ID NO: 27 is C L S X G S S C S; and SEQ ID NO: 28 is Y N C C R S C N X Y S R K C R.

5. Considering both active groups together, amino acid positions which are conserved in all active species are preserved. Thus, for example, the Cys residues, the 5-position glycine, the 13-position tyrosine, the 19-position serine, and the 26-position lysine are all preserved. Preferred OCT analogs or derivatives may be selected by comparing, for purposes of inter-sequence conservation and substitution, those sequences known to be active. For example, in the case of the treatment of pain, omega-conopeptides MVIIA (SNX-111) and TVIA (SNX-185) are known active compounds. Active derivatives are those peptides having, in addition to the conserved cysteine residues described above, a conserved glycine residue at position 5, conserved serine residues at positions 9, 19, and 24, and a conserved lysine residue at position 26. Inter-sequence substitution of variable residues is then preferable in the formation of active analogs. For example, analog position 2 may be occupied by a lysine or a leucine residue, and position 6 may be occupied by an alanine or a serine residue.

6. Considering both active groups together, there are amino acid positions which are likely to be variable within the range of active species. For example, the position 2 amino acid may be lysine or leucine, the position-3 amino acid may be glycine or serine, and the position 4 amino acid, hydroxyproline or arginine. In addition, if the two or more amino acids at a variant position are in a common substitution class, substitution within that class may be favorable. Standard substitution classes are the six classes based on common side chain properties and highest frequency of substitution in homologous proteins in nature, as determined, for example, by a standard Dayhoff frequency exchange matrix (Dayhoff). These classes are Class I: Cys; Class II: Set, Thr, Pro, 4Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoarginine, N-methyl lysine, dimethyl lysine, or trimethyl-lysine in class IV, and a halogenated tyrosine in Group VI. Further, the classes may include both L and D stereoisomers, although L-amino acids are preferred for substitutions.

7. Considering the known inactive species, substitutions to amino acids which are present in inactive species, but not active ones, at any selected residue position, are not favored to preserve activity in the active compounds. Thus, for example, although a 3-position serine is present in both active and inactive compounds, 4-position serine or threonine is present in inactive species only, and either substitution is thus disfavored.

The above amino acid selection rules 6–7 are intended as a guide for allowed amino acid substitutions within active omega-conopeptides. Once an amino acid substitution or modification is made, the peptide is further screened for the requisite calcium channel antagonist activity, and the requisite activities for inhibition of neurotransmitter release and binding to the appropriate OCT binding site of neuronal membranes, as described above.

Several of the amino acid substitutions or modifications to the omega-conopeptide illustrate the principles outlined above.

Omega-conopeptides which are selected on the basis of these criteria, discussed in detail below, are tested for ability to produce or enhance analgesic effects produced by sub-maximal doses of opioid compounds in a standard test of analgesia, such as the Rat Tail-Flick test, wherein analgesia is measured by a prolongation of reaction time to a noxious radiant heat stimulus.

B. In Vitro Properties of Analgesic Omega-conopeptides

1. Calcium Channel Blocking Activity

Calcium channel blocking activity was measured electrophysiologically in neuronal (N1E-115 or IMR-32) cell lines, as described in Section II, above, and in detail in Example 1. Omega-conopeptides having calcium channel blocking activity are those which block calcium currents in such cell lines with potencies in the range observed for omega-conopeptides MVIIA and GVIA in N1E-115 cells, or displaying the efficacy observed for omega-conopeptides MVIIA and SVIB in IMR-32 cells (FIG. 5C).

2. High Affinity Binding to OCT Binding Sites

Methods for determination of binding affinity to OCT binding sites are discussed in Examples 2-4, below.

Experiments testing reversibility of binding of SNX-111, SNX-183 and SNX-124 revealed that SNX-111 and SNX-183 exhibited dissociation half-times of two and five minutes, respectively. In contrast, SNX-124 did not dissociate appreciably from its binding site(s), even 1 hour following addition of excess unlabelled compound.

Compounds were tested for their ability to displace binding of SNX-111 or SNX-183 from their respective binding sites. In displacing SNX-111, it was found that compounds which produce or enhance opioid antinociceptive activity, such as OCT MVIIA (SNX-111), and TVIA (SNX-185), have $IC_{50}$ values between about 15 and 300 pM, and $K_i$ values between about 1 and 100 pM. In contrast inactive compound SNX-183 had an $IC_{50}$ of greater than 1000 pM for binding at the MVIIA site. MVIIC (SNX-230/SNX-231) showed $IC_{50}$ values which were lower than that of SNX-185; however, MVIIC (SNX-230) was shown to be inactive in inhibiting contractions of the guinea pig ileum, as discussed below, and is therefore not a candidate for an antinociceptive compound of the invention.

From the foregoing, it is seen that active compounds in accordance with the invention are characterized by a high binding affinity for MVIIA binding site 1. The binding affinity for these sites may be characterized as follows. In the first approach, the binding affinity of the compound for the MVIIA site, as estimated by $IC_{50}$ at the site, is compared directly with those of selected high affinity active compounds, such as SNX-111 and SNX-185. An active compound is one whose binding affinity is at least as high as and preferably within the range of binding affinities measured for such high affinity OCT's. Secondly, the binding affinity of the test compound can be characterized by binding to SVIB binding site 2, as described above for binding to MVIIA binding site 1. Thirdly, the binding affinity of the compound can be characterized by the ratio of binding constants or relative potencies of the compound for the MVIIA and SVIB sites, as just described. Here an active compound is one whose binding ratio is within the range for the selected active peptides, such as MVIIA (SNX-111) and TVIA (SNX-185); i.e., the binding ratio is substantially within the range of the ratio observed for the omega-conopeptides MVIIA and TVIA.

A number of omega-conopeptide compounds which were tested gave $IC_{50}$ and $K_i$ values lower than or within the ranges of those of omega-conopeptides MVIIA (SNX-111) and TVIA (SNX-185) for binding at the SNX-111 site, and these compounds should thus be considered candidates as antinoceceptive and antinociceptive enhancing compounds. However, some of these compounds, may not fulfill additional criteria for anti-nociceptive compounds of the invention, as described herein.

3. Localization of OCT Binding in the Central Nervous System

Conopeptide SNX-111 binds to distinct regions of the brain and spinal cord which are commonly associated with pain pathways (FIG. 12). These include the periaquaductal grey (PAG) region of the brain and the dorsal horn of the spinal cord. The distribution of CgTx (GVIA) binding shown by Takemura et al (1989) also shows localization of CgTx binding sites at a very high level in the dorsal horn of the spinal cord ($1^{st}$ and $2^{nd}$ layers of Rexed) and, to a lesser degree, in the central grey region of the mesencephalon, which may correspond to the PAG.

4. Inhibition of Neurotransmitter Release

Another requisite property of anti-nociceptive OCT compounds, in accordance with the invention, is their ability to specifically inhibit depolarization-evoked and calcium-dependent neurotransmitter release from neurons. In the case of anti-nociceptive omega-conopeptides, inhibition of electrically stimulated release of acetylcholine at the myenteric plexus of the guinea pig ileum (Example 6E) is predictive of anti-nociceptive activity, as seen in Table 10. Omega-conopeptides having anti-nociceptive activity and/or anti-nociceptive enhancing activity have $IC_{50}$'s in the range of those values observed for active omega-conopeptides MVIIA (SNX-111) and TVIA (SNX-185), or less than approximately 50 nM, as shown in this assay.

5. In Vivo Measurements of Analgesia

Analgesia is conveniently measured in one or more of a number of animal models, in which an animal's response to a given pain stimulus is measured. One such model is the Rat Tail-Flick test, described in Example 7. Briefly, in this test, a rat is positioned such that its tail is exposed to a standard heat source, and the time that the animal voluntarily endures the heat, prior to moving its tail, is recorded. Analgesics, particularly opioid analgesics, prolong this time.

Figure 15:
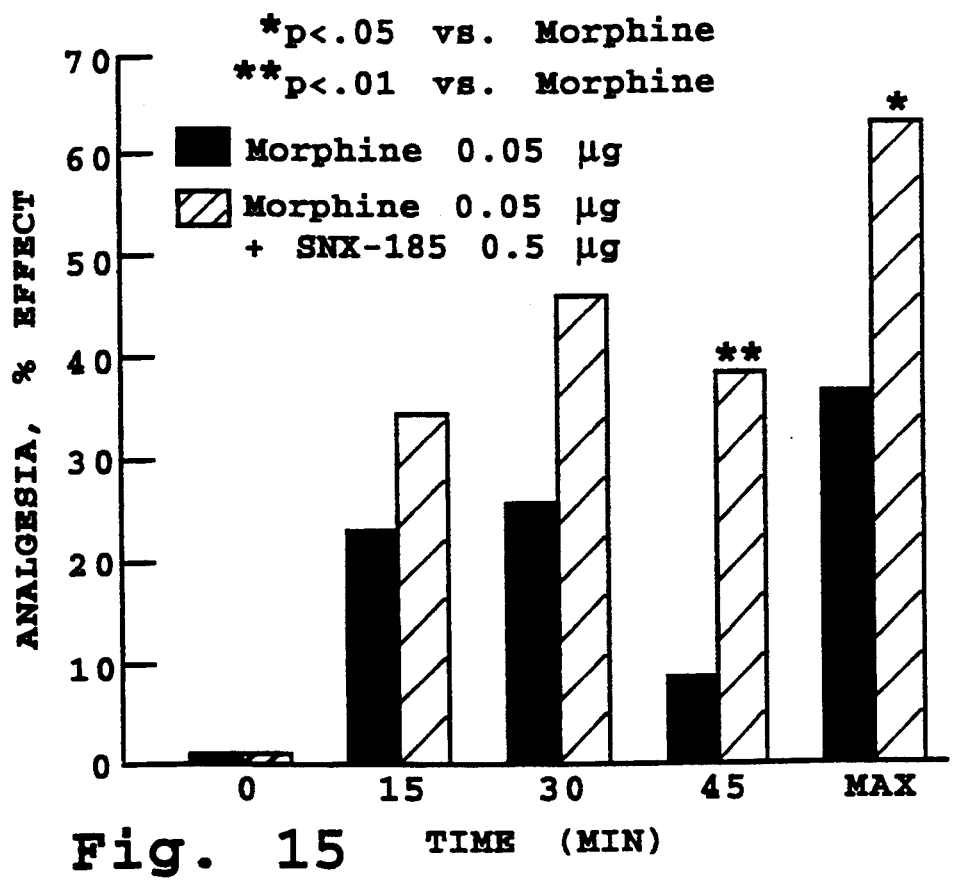
FIG. 15 shows the production of analgesia by a submaximal intrathecal dose of morphine (0.5 μg) administered alone (solid bars) and in the presence of 0.5 μg SNX-111 (hatched bars)

Shown in FIG. 15 are the results of experiments in which the effects of a sub-maximal dose of morphine were compared to those of the combination of a sub-maximal dose of morphine and a 0.5 μg (intrathecal) dose of SNX-185 in the Rat Tail-Flick Test. Animals were tested at various time points following injection, as indicated, and latency of tail-flick recorded. In addition, for each animal, the maximum latency response (regardless of time after administration) was recorded, and the mean of such maximal responses calculated as the maximal percent effect (MPE). Intrathecal administration of SNX-185 enhanced the effects of a sub-maximal dose of morphine (FIG. 15) in this assay at all time points, and significantly at 45 min. after administration of compound. By the term "submaximal dose" is meant a dose of morphine or other opiate which is insufficient to induce maximal latency of response in the tail-flick assay, measured as Percent Effect, the calculation of which is described in Example 7.

Additional experiments summarized in Tables 11A and 11B show the effects of SNX-185 given alone or in combination with varying doses of morphine administered 1 hour later, shown on the right side of the table. SNX-185 showed a significant analgesic effect when given alone at a dose of 0.5 μg, in at least two of the trials. Groups of animals injected with SNX-185 also generally showed greater responses to subsequent injection of a low dose (0.05 μg) of morphine (Table 11A).

In separate experiments (Tables 12A and 12B), SNX-111 (0.1 μg) and SNX-185 (0.05 μg) enhanced the effects of submaximal doses of morphine, whereas SNX-124 (0.1 μg) had no effect. SNX-183 (1 μg) showed a small but measurable effect, but this effect was not significant when compared to control.

TABLE 11A

Effect of SNX-185 ± Morphine on Latency Percent Effect in Rat Tail-Flick Assay

| SNX-185 Dose (μg) | n | Time After Injection (min) % Effect (± SE) 25 | Time After Injection (min) % Effect (± SE) 45 | Morphine Dose (μg) | Time After Injection (min) % Effect (± SE) 25 | Time After Injection (min) % Effect (± SE) 45 |
|---|---|---|---|---|---|---|
| 0 | 6 | 20 ± 16 | 18 ± 12 | 0.2 | 58 ± 22 | 66 ± 17 |
| 0.5 | 7 | 29 ± 13 | *57 ± 13 | 0.2 | 98 ± 2 | 92 ± 5 |
| 0 | 8 | 16 ± 15 | 12 ± 14 | 0.1 | 61 ± 15 | 75 ± 11 |
| 0.5 | 9 | 0 ± 4 | 13 ± 11 | 0.1 | 60 ± 17 | 51 ± 17 |
| 0 | 5 | 9 ± 5 | 8 ± 3 | 0.1 | 45 ± 20 | 49 ± 16 |
| 0.5 | 5 | 12 ± 10 | 8 ± 3 | 0.1 | 79 ± 21 | 77 ± 21 |
| 1.0 | 4 | 33 ± 22 | 36 ± 20 | 0.1 | — | — |
| 0 | 8 | 1 ± 3 | 5 ± 2 | 0.05 | 7 ± 6 | 16 ± 11 |
| 0.5 | 8 | *27 ± 11 | 14 ± 7 | 0.05 | *44 ± 16 | 30 ± 18 |

*p < .05 vs. Control.

TABLE 11B

Effect of SNX-185 ± Morphine on Latency Percent Effect in Rat Tail-Flick Assay

| | Time After Injection (Sal. or 185) | | | | Time After Injection (0.05 μg morphine) | | | |
|---|---|---|---|---|---|---|---|---|
| | 15 | 30 | 45 | MPE | 15 | 30 | 45 | MPE |
| Saline (n = 16) | | | | | | | | |
| Mean | 2 | 1 | 3 | 14 | 17 | 19 | 18 | 26 |
| SE | 6 | 6 | 7 | 7 | 10 | 9 | 9 | 9 |
| SNX-185, 0.5 μg (n = 17) | | | | | | | | |
| Mean | 9 | *17 | 14 | 26 | 37 | 33 | 26 | 41 |
| SE | 4 | 4 | 6 | 5 | 11 | 11 | 10 | 11 |

*p < .05 vs. control.

TABLE 12A

Effect of Coadministration of Conopeptides and Morphine on Analgesia (% Effect) in Rat Tail-Flick Assay

| | Time After Injection | | | |
|---|---|---|---|---|
| | 15 | 30 | 35 | MPE |
| Morphine, 0.05 μg (n = 14) | | | | |
| Mean | 15 | 13 | 7 | 23 |
| SE | 7 | 6 | 5 | 8 |
| SNX-111, 0.1 μg + morphine (n = 13) | | | | |
| Mean | 12 | 33 | *38 | 42 |
| SE | 9 | 10 | 12 | 11 |
| SNX-124, 0.1 μg + morphine (n = 14) | | | | |
| Mean | *−7 | 5 | 11 | 14 |
| SE | 5 | 6 | 11 | 8 |
| SNX-183, 1.0 μg + morphine (n = 14) | | | | |

TABLE 12A-continued

Effect of Coadministration of Conopeptides and Morphine on Analgesia (% Effect) in Rat Tail-Flick Assay

| | Time After Injection | | | |
|---|---|---|---|---|
| | 15 | 30 | 35 | MPE |
| Mean | 18 | 31 | 25 | 39 |
| SE | 6 | 8 | 6 | 7 |

*p < .05 vs. morphine alone.

TABLE 12B

Effect of Coadministration of SNX-185 and Morphine on Analgesia (% Effect) in Rat Tail-Flick Assay

| | Time After Injection | | | |
|---|---|---|---|---|
| | 15 | 30 | 35 | MPE |
| Morphine, 0.05 μg (n = 10) | | | | |
| Mean | 14 | 18 | 13 | 23 |
| SE | 8 | 11 | 9 | 10 |
| Morphine, 0.05 μg, plus SNX-185, 0.5 μg (n = 10) | | | | |
| Mean | *51 | 48 | 41 | 55 |
| SE | 14 | 14 | 15 | 13 |

*p < .05 vs. morphine alone.

Figure 16A:
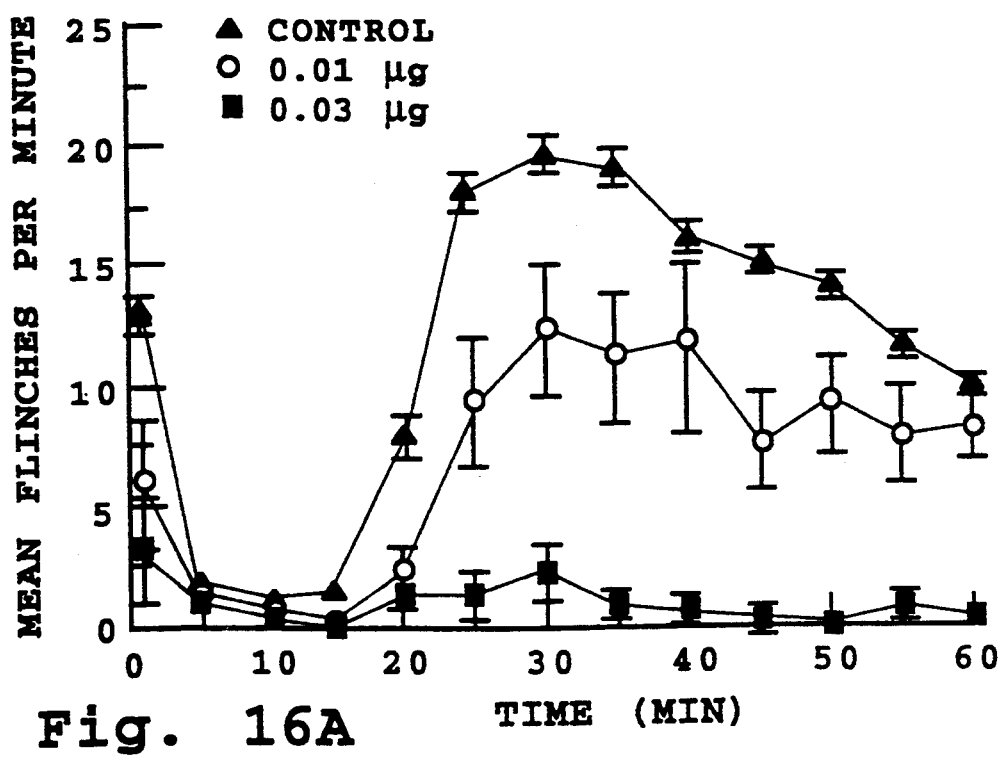
FIG. 16 (A–C) shows effects of SNX-111(A), SNX-185(B) and SNX-231(C) on flinch response in rat formalin tests.
Figure 16B:
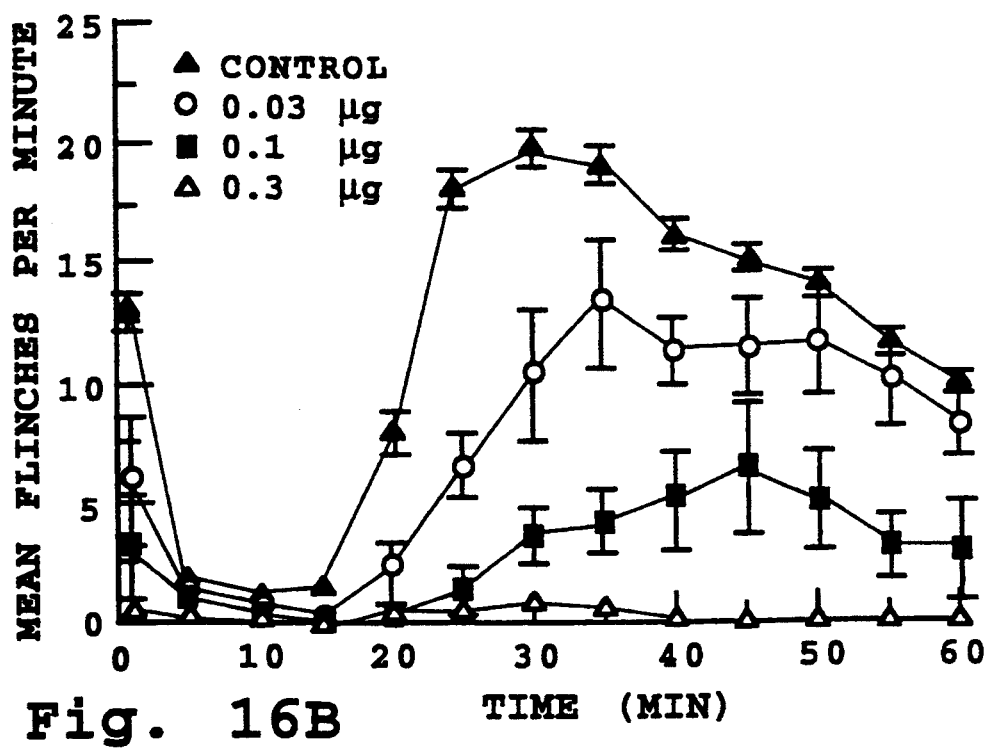
Figure 16C:
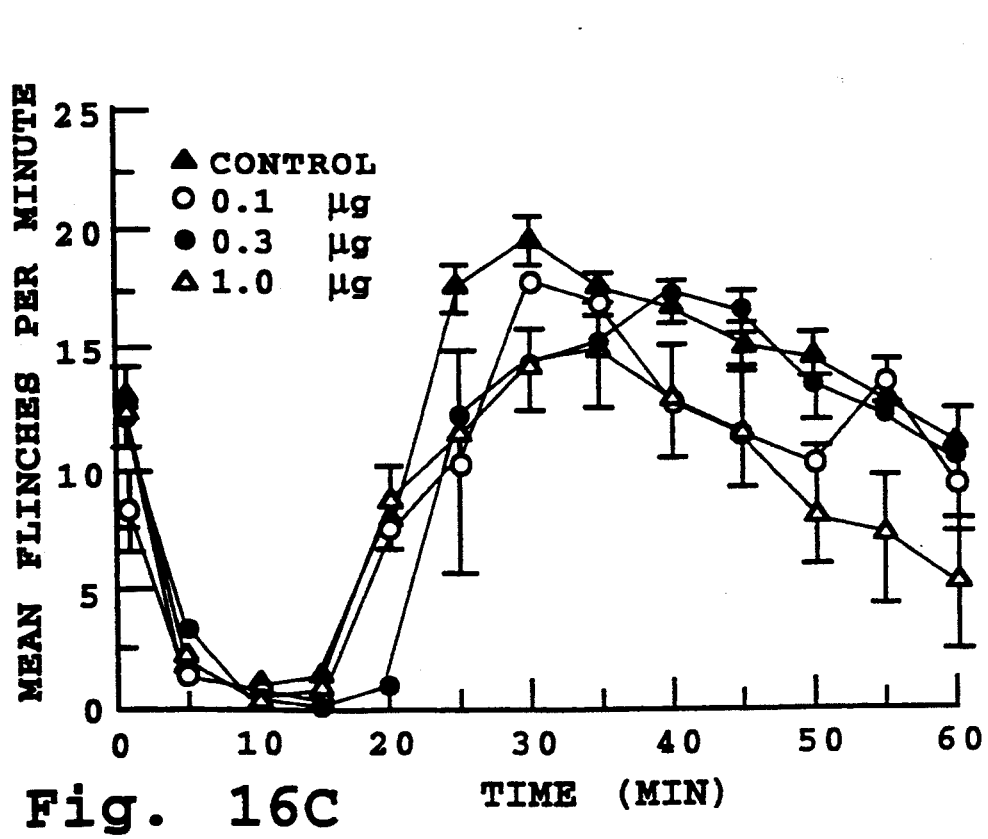

Another in vivo test of analgesic potency is the rat formalin test. Briefly, in this test, a standard dose of formalin is injected into the rat paw, and flexions of the paw are quantitated. Typically in this assay a biphasic response pattern is observed, with numerous responses observed during the period 5 min. after injection (Phase 1) and a second phase (Phase 2) which occurs during the period about 10–60 minutes following injection (FIG. 16). Quantitation of responses during each phase is made by calculation of area under the curve of flinches/min. as described in Example 8.

Figure 17A:
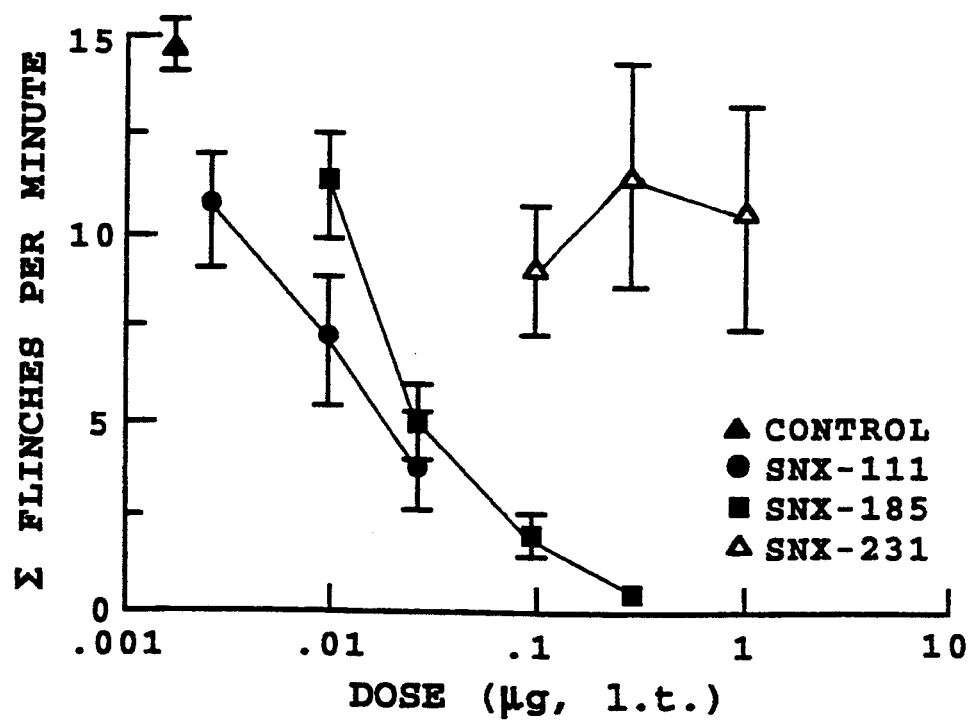
FIGS. 17A and 17B shows log dose response curves for effects of SNX-111 (CTX A; closed circles), SNX-185 (CTX B; closed squares) and SNX-231 (CTX C; open triangles) on phase 1(A) and phase 2(B) of the formalin test.
Figure 17B:
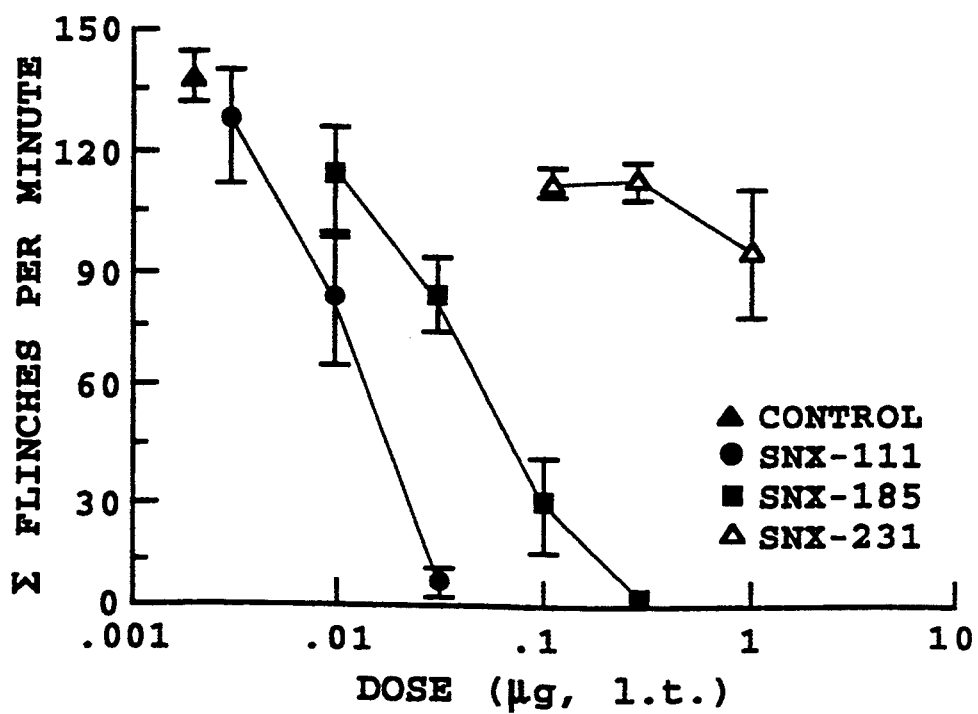

FIG. 17 shows results of experiments in which SNX-111, SNX-185 and SNX-231 were tested for effects on the formalin response in rats. From the curves shown, doses which resulted in approximately 50% inhibition in Phase 1 and Phase 2 responses were determined (Table 13). As shown in FIG. 16, administration of SNX-111 and SNX-185 each resulted in dose dependent inhibition of both Phase 1 and Phase 2 response evoked by formalin. SNX-231 was without effect at the doses employed in the assay.

TABLE 13

ED Values for Intrathecal Administration of Conopeptides on Phase 1 and Phase 2 of the Formalin Test

| Drug | N | Phase 1 | Phase 2 |
|---|---|---|---|
| SNX-111 | 21 | 0.009 μg | 0.013 μg |
| SNX-185 | 20 | 0.02 μg | 0.05 μg |
| SNX-231 | 12 | >1.0 μg | 1.0 μg |

III. Treatment of Other Neurogenic Disorders

As indicated above, conopeptides such as MVIIA and TVIA, and their derivatives, have a number of peptide-specific binding/inhibitory activities, which include:

(1) high-affinity binding to the MVIIA binding site of neuronal cells;
(2) inhibition of norepinephrine release in central nervous system neuronal cells;
(3) inhibition of voltage-gated calcium channels selectively in neuronal tissue, as evidenced by the inhibition of electrically stimulated contraction of the guinea pig ileum; and
(4) inhibition (blockage) of membrane currents associated with N-type or omega HVA neuronal calcium channels in an isolated cell system, such as the mouse neuroblastoma cell line;

Previously it has been shown (co-owned U.S. Pat. No. 5,051,403) that conopeptides having defined binding/inhibitory activities are effective in reducing neuronal damage related to an ischemic condition in mammals. The binding/inhibitory activities of conopeptides effective in such treatment include:

(a) high-affinity binding to the MVIIA binding site; and
(b) inhibition of norepinephrine release in central nervous system neuronal cells.

Two conopeptides which have these characteristic activities, and which have been shown effective in reducing post-ischemia neuronal damage, are conopeptides MVIIA and TVIA.

In the section above, it was shown that conopeptides, such as MVIIA and TVIA, which have defined binding/inhibitory activities, are effective in producing and enhancing analgesia by opiates. The important binding/inhibitory activities are:

(a) high-affinity binding to the MVIIA binding site; and
(b) inhibition of voltage-gated calcium channels selectively in neuronal tissue, as evidenced by the inhibition of electrically stimulated contraction of the guinea pig ileum.

It is of interest, therefore, to show that conopeptides such as MVIIA, TVIA and derivatives thereof having (a) high-affinity binding to the MVIIA binding site of neuronal cells, and (b) a cell-inhibitory activity related to the inhibition of N-channel calcium currents, are also effective as therapeutic agents against a variety of other neurogenic conditions, as follows:

A. Schizophrenia

Schizophrenia is a neurogenic disorder which is currently treated primarily with compound such as phenothiazines and butyrophenones, which block dopamine receptors.

The in vitro selection criteria for omega-conopeptides useful in treating schizophrenia include: a) blockade of voltage-gated calcium channels, b) high affinity reversible binding to an omega-conopeptide binding site localized to the limbic region of the brain, and c) inhibition of dopamine release from brain regions, particularly limbic brain regions.

Compounds showing sufficiently high activities in the above in vitro screening assays are then tested in an animal model used in screening anti-psychotic compounds, the rat striatal turning model. In the paradigm used, animals are subjected to unilateral lesion of the nigrostriatal pathway in the brain, by application of 6-hydroxydopamine to this pathway. Lesioned animals characteristically display a turning or circling behavior, with turning occurring in the direction ipsilateral to the lesioned side. Compounds useful in the treatment method of the invention, when injected locally to the striatum contralateral to the lesion, will correct the circling behavior.

B. Tardive Dyskinesia and Acute Dystonic Reactions

Tardive dyskinesia and acute dystonic reactions are movement disorders which are commonly produced as side effects of anti-psychotic therapy employing dopamine antagonists, such as haloperidol. These disorders are characterized by supersensitivity of dopamine receptors in certain regions of the brain associated with control of movement, particularly the basal ganglia. Currently, intermittent antipsychotic therapy is used in attempts to avoid onset of the disorder, and such disorders are treated by withdrawal of therapy.

Criteria for selection of an omega-conopeptide for treatment of tardive dyskinesia include: a) blockade of voltage-gated calcium channels, b) high affinity reversible binding to the OCT MVIIA peptide binding site localized to the basal ganglia, c) inhibition of dopamine release from striatal brain regions, and other regions of the basal ganglia, and d) a ratio of inhibition of dopamine release in the basal ganglia to inhibition of dopamine release in the limbic regions which is within the range of such ratio observed for SNX-111.

Compounds showing sufficiently high activities in the above in vitro screening assays are then tested in the rat striatal turning model, described above. Compounds useful in the method of treating such movement disorders, when injected to the striatum on the side of the brain contralateral to the lesion, correct the turning behavior.

C. Inflammation

A neurogenic component of inflammation has been described, in that blockade of the sympathetic nervous system, and particularly blockade of beta-adrenergic receptors, is helpful in reducing inflammatory joint damage. Compounds useful in the treatment of inflammation would be expected to have the following in vitro properties: a) blockade of voltage-gated calcium channels, b) high affinity binding to the omega-conopeptide binding sites, and c) inhibition of norepinephrine release from nervous tissue. Compounds exhibiting sufficiently high activities in such in vitro screening assays are tested in an animal model of rheumatoid arthritis, such as that described by Fitzgerald (1989).

The following examples are intended to illustrate various characteristics of the method of the invention, but are in no way intended to limit the scope of the invention.

EXAMPLE 1

Calcium Channel Antagonist Activity: Inhibition of Ionic Currents

Ionic currents through calcium channels were examined in cells that were voltage-clamped by a single patch-clamp electrode. These whole-cell patch-clamp studies were performed mainly on N1E115 mouse neuroblastoma cells, although a variety of cell types, including human neuroblastoma cell line IMR-32, have been examined.

A. Current Measurement Methods

Most measurements were obtained using a bath saline that allowed examination of the calcium currents in the absence of other ionic currents. These solutions contained 80 mM NMDG (as a sodium replacement), 30mM TEACl (to block potassium currents), 10 mM $BaCl_2$ (as a charge-carrier through the calcium channels), and 10 mM HEPES at pH 7.3. Some solutions also contained 2 mM quinidine (to block potassium currents) and 3 $\mu$M tetrodotoxin (to block sodium currents). Normal bath saline was (mM): 140 NaCl, 10 glucose, 3 KCl, 2 $CaCl_2$, 1 $MgCl_2$, 10 mM HEPES pH 7.3. Intracellular solutions contained 150mM CsCl, 0.5 mM $CaCl_2$, 5 mM EGTA, 5 mM $MgCl_2$, 2 mM $K_2ATP$ at pH 7.3–7.4. Bath saline and all internal solutions were filtered before use.

Pipets were made from Corning 7052 glass (Garner Glass Company, Claremont, Calif. 91711), coated with Sylgard (Dow Corning, Midland, Mich. 48640) and fire-polished before use. Bubble numbers were typically 5 to 6, with pipet resistances typically 2–5 MOhms. Corning 8161, Kimble, and other glasses were also used without noticeable effect on the calcium currents observed.

Recordings were carried out at room temperature with an Axopatch 1-C amplifier (Axon Instruments, Foster City, Calif. 94404) and analyzed with pCLAMP software (Axon Instruments). Data were filtered at 1000 Hz for a typical sampling rate of 0.1 kHz; in all cases data were filtered at a frequency at most 1/5 of the sampling rate to avoid biasing. Data were collected on-line by the software. Analysis was performed on-screen with print-out via a Hewlett-Packard LaserJet Printer (Hewlett-Packard, Palo Alto, Calif. 94306).

The typical experiment was conducted as follows: after seal formation followed by series resistance compensation and capacitative transient cancellation, a voltage clamp protocol was performed wherein the cell potential was stepped from the holding potential (typically $-100$ mV) to test potentials that ranged from $-60$ mV to $+20$ mV in 10 mV increments. The cell was held at the holding potential for 5 seconds between pulses. Protocols starting from other holding potentials usually covered the same range of test potentials.

B. Current Inhibition Measurement

FIG. 3 shows calcium current traces from an N1E-115 mouse neuroblastoma cell. The figure is read from left to right in time, with downward deflections of the trace indicating positive current flowing into the cell. Currents were elicited by a voltage step from 100 mV to $-10$ mV. The cell was bathed in saline with sodium replaced by NMDG and 10 mM $Ba^{++}$ instead of 2 mM $Ca^{++}$. Potassium currents were blocked by TEA in the bath and $Cs^+$ in the pipet solution.

The three traces in FIG. 3, labeled B–D, show decreasing calcium currents, with increasing MVIIA omega-conopeptide concentrations of 10 nM (3B), 50 nM (3C), and 200 nM (3D).

The response of voltage-gated calcium current to increasing dosages of OCTs MVIIA and GVIA are shown in FIG. 4. The calculated $IC_{50}$ is approximately 10 nM for GVIA and 100 nM for MVIIA. These values indicate extremely high specificity of the peptides for their site of action.

Table 1 compares $IC_{50}$ values for GVIA, MVIIA, SVIB and SVIA OCTs. Whereas OCT GVIA and OCT MVIIA show 50% inhibition of the measured calcium current at nanomolar concentration range, $IC_{50}$ values for OCT SVIB and OCT SVIA were not measurable within the range of concentrations tested, and are therefore listed as having $IC_{50}$ values above the micromolar concentrations indicated.

EXAMPLE 2

Synaptosomal Membrane Preparations

A. Mammalian Brain Synaptosomes and Synaptosomal Membranes

Synaptosomes were prepared from rat whole brain or hippocampal region of brain. Rats were sacrificed, and forebrains were removed and transferred to 10 ml ice-cold 0.32 M sucrose containing the following protease inhibitors (PI): 1 mM EGTA; 1 mMEDTA; 1 uM pepstatin; 2 uM leupeptin. Brains were homogenized using a motor-driven Teflon-glass homogenizer (approx. 8 passes at 400 rpm). Homogenates from 4 brains were pooled and centrifuged at 900 xg for 10 minutes at 4 degrees. Supernatants were then centrifuged at 8,500 xg for 15 minutes. Resulting pellets were resuspended in 10 ml each ice-cold 0.32 M sucrose plus PI with vortex mixing. The suspension was then centrifuged at 8,500 xg for 15 minutes. Pellets were resuspended in 20 ml ice-cold 0.32 M sucrose plus PI. The suspension (5 ml/tube) was layered over a 4-step sucrose density gradient (7 ml each: 1.2 M sucrose, 1.0 M sucrose, 0.8 M sucrose, 0.6 M sucrose; all sucrose solutions containing PI). Gradient tubes were centrifuged in a swinging bucket rotor at 160,000 xg for 60 minutes at 4 degrees. The 1.0 M sucrose layer plus the interface between the 1.0 and 1.2 M sucrose layers were collected and diluted with ice cold deionized water plus PI to yield a final sucrose concentration of 0.32 M. The resulting suspension was centrifuged at 20,000 xg for 15 minutes. Pellets were then resuspended in 5 ml ice-cold phosphate buffered saline plus PI. The resulting rat brain synaptosomes were then aliquoted and stored in a liquid nitrogen containment system.

Prior to use in binding assays, synaptosomes were thawed and diluted with 3 volumes of ice cold deionized water plus PI. This suspension was homogenized using a PT 10-35 Polytron (setting 6) for two 10-second bursts. The homogenate was centrifuged at 40,000 xg for 20 minutes at 4 degrees. The resulting pellets were resuspended in about 5 ml of ice cold phosphate buffered saline plus PI. The resulting brain synaptosomal membrane preparation was aliquoted and stored at −80° C. until use. Protein concentration of the membrane preparation was determined using Bradford reagent (BioRad), with bovine serum albumin as standard.

B. Electric Organ Synaptosomes

Electric organ synaptosomes were prepared by dissection from marine electric rays (*Ommata dyscopyge* or *Narcine brasiliensis*) that had been stunned with 0.25 g/liter tricaine HCl and cooled to 4° C. immediately prior to dissection. All subsequent manipulations were carried out at 0°-4°C. whenever possible. Organs were diced and homogenized for 4 15-second periods in a Waring blender with an equal weight of synaptosome buffer (SB) (20 mM HEPES, Ph 7.2, 280 mM NaCl, 3 mM KCl, 1.8 mM MgCl₂, 300 mM urea, 100 mM sucrose, 5.5 mM glucose plus protease inhibitors), (1 mM EGTA, 1 μM pepstatin, 2 μM leupeptin, 1 μg/ml aprotinin and 0.1 mg/ml bacitracin).

The homogenate was filtered through cheesecloth and centrifuged at 30,000 xg for 15 min. The supernatant was discarded and each pellet was taken up in 10 ml synaptosome buffer plus protease inhibitors. The resuspended pellets were combined and further disrupted with 5 strokes of a Teflon pestle in a glass homogenizer set at 400 rpm. The resulting suspension was centrifuged at 30,000 x g for 15 min. The supernatant was discarded and the pellet resuspended in approximately 5 ml of SB with protease inhibitors using a Teflon-glass homogenizer. This homogenate was layered onto six 32 ml 3-20% Ficoll gradients in SB (no protease inhibitors) and centrifuged at 100,000 x g for 1 hour in a swinging bucket rotor. The synaptosome band (the first band below the buffer-gradient interface) of each gradient was aspirated off and diluted 2:1 with synaptosome buffer with protease inhibitors. The diluted synaptosome suspension was pelleted at 30,000 x g for 15 min and resuspended in synaptosome buffer and refrigerated, for use in ATP release assays within 2 days of preparation. For binding experiments, aliquots were frozen at −160°.

EXAMPLE 3

Omega-conopeptide Binding to Omega-conopeptide Binding Sites in Synaptosomal Membranes A. Saturation Binding Assay MVIIA OCT was radiolabeled with $^{125}$I-iodine by reaction with Iodogen ®, essentially according to the method of Ahmad and Miljanich. Following the Iodogen reaction, the peptide solution was chromatographed by HPLC through a C-8 reversed phase column and eluted with a gradient from 0.1% trifluoroacetic acid in water to 0.1% trifluoroacetic acid in water/acetonitrile (40:60 vol/vol). The major peak of radioactivity following the underivatized MVIIA OCT was collected.

Figure 6B:
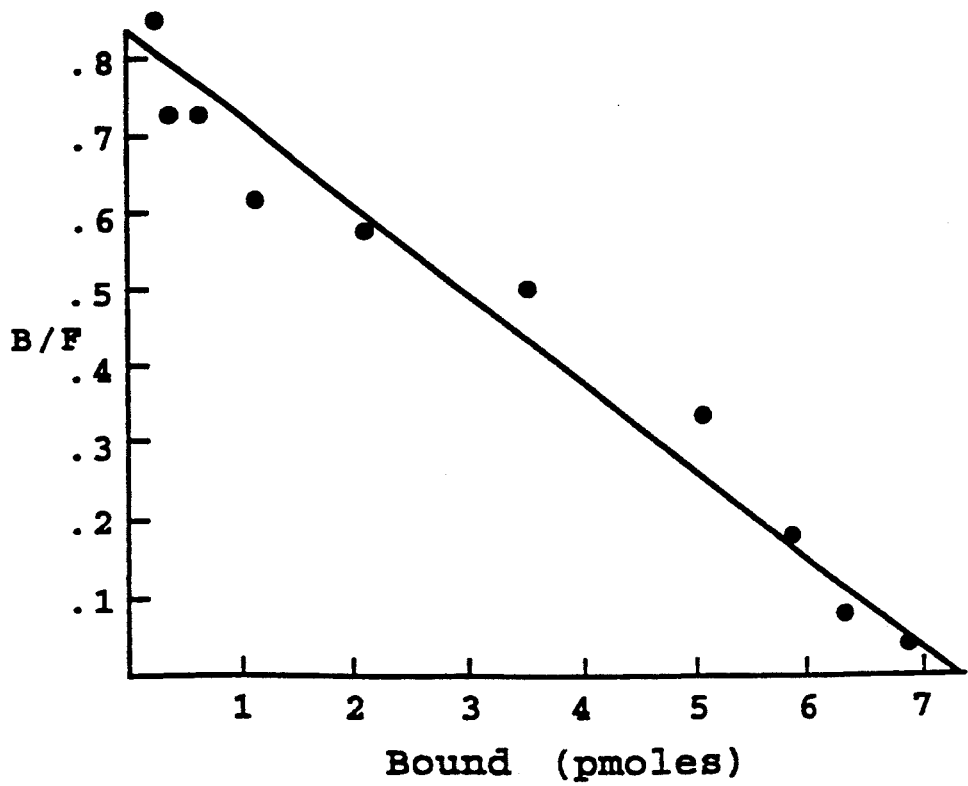

The binding constant ($K_d$) for [$^{125}$I]MVIIA OCT to rat brain synaptosomal membranes was determined by a saturation binding method in which increasing quantities of [$^{125}$I]MVIIA OCT were added to aliquots of a synaptosomal membrane preparation (10 ug membrane protein, suspended in binding buffer consisting of 20 mM HEPES, pH 7.0, 75 mM NaCl, 0.1 mM EGTA, 0.1 mM EDTA, 2 μM leupeptin, 0.035 μg/ml aprotinin, and 0.1% bovine serum albumin (BSA), in a total volume of 0.5 ml). Binding at each concentration of labeled compound was determined in the absence and presence of 1 nM unlabeled MVIIA OCT to determine specific binding (as described in part B, below). The amount of labeled peptide specifically bound at each concentration was used to determine $B_{max}$, the concentration of specific binding sites on the synaptosomes, and $K_d$, following standard binding analysis methods (Bennett). FIG. 6A shows a saturation binding curve of [$^{125}$I]MVIIA to rat synaptosomal membranes. FIG. 6B shows a Scatchard transformation of the data, from which a calculated $K_d$ of about 10 pM is determined.

B. Reversibility of Binding

Rat brain synaptosomal membranes were incubated with a concentration of radiolabeled ligand approximating the $K_d$ of the ligand for its binding site, for a period of time sufficient to achieve equilibrium binding. A high concentration of unlabeled ligand was then added to the mixture, and the incubation continued. At time intervals, samples of the mixture were tested for binding of radiolabeled compound. As shown in FIG. 7, SNX-111 exhibited reversible binding with a dissociation half-time of about 2 min. Likewise, SNX-183 binding exhibited reversible binding with a dissociation half-time of about 5 min. In contrast, radiolabeled SNX-124 showed no dissociation from its binding site over the time period studied (60 min).

C. Competitive Displacement Binding Assay

1. Competitive Displacement of OCT MVIIA

Rat brain synaptosomal membranes prepared as described in Example 2 were suspended in a binding buffer consisting of 20 mM HEPES, pH 7.0, 75 mM NaCl, 0.1 mM EGTA, 0.1 mM EDTA, 2 μM leupeptin, 0.035 μg/ml aprotinin, and 0.1% bovine serum albumin (BSA). [$^{125}$I]-MVIIA (SNX-111) OCT (25–30,000 cpm, approximately 1500–2000 Ci/mmol) and test compound were aliquoted into polypropylene tubes, in the absence or presence of 1 nM MVIIA (SNX-111) OCT to determine non-specific binding. The membrane suspension was diluted and aliquoted last into the test tubes, such that each assay tube contained 10 μg membrane protein and the total volume was 0.5 ml. After incubation for 1 hour at room temperature, tubes were placed in an ice bath, then filtered through GF/C filters (Whatman), which were presoaked in 0.6% polyethyleneimine and prewashed with wash buffer (20 mM HEPES, pH 7.0, 125 mM NaCl, 0.1% BSA) using a Millipore filtration system. Just prior to filtration, each assay tube received 3 ml ice-cold wash buffer. The filtered membranes were washed with two 3 ml volumes of ice-cold wash buffer, dried, and filter-bound radioactivity was measured in a Beckman gamma counter (75% counting efficiency).

Representative displacement binding curves for rat brain synaptosomal membranes are illustrated in FIG. 8. $IC_{50}$ values were computed from line fit curves generated by a 4-parameter logistic function. These values represent the concentration of test compound required to inhibit by 50% the total specific binding of $[^{125}I]$-MVIIA (SNX-111) OCT to rat brain synaptosomal membranes, where specific binding is defined as the difference between binding of $[^{125}I]$-MVIIA (SNX-111) OCT in the absence and presence of excess (1 nM) unlabelled MVIIA OCT. Non-specific binding is that binding of radiolabeled compound which is measured in the presence of excess unlabeled MVIIA OCT. Such values serve as approximations of the relative affinities of a series of compounds for a specific binding site.

2. Competitive Displacement of OCT SVIB

Rat brain synaptosomal membranes were prepared as described in Example 2. OCT SVIB was radiolabeled by iodination with $^{125}I$-iodine by the Iodogen reaction, described in Example 3. Displacement binding of radiolabeled SVIB on rat brain synaptosomal membranes was carried out as in Example 4B. SVIB displacement curves for several of the omega-conopeptides assayed is shown in FIG. 9. $IC_{50}$ values and relative potency values were calculated as described below. Table 4 shows the relative potency values for omega-conopeptides examined, and the ratio of relative potencies of the compounds for the OCT MVIIA site and to the SVIB binding site.

The binding constant ($K_i$) for each test substance was calculated using non-linear, least-squares regression analysis (Bennett & Yamamura) of competitive binding data from 2 assays performed in duplicate on separate occasions. The relationship between $K_i$ and $IC_{50}$ (concentration at which 50% of labeled compound is displaced by test compound is expressed by the Cheng-Prusoff equation:

$$K_i = IC_{50}/(1+[L]/K_d)$$

where $IC_{50}$ is the concentration of test substance required to reduce specific binding of labeled ligand by 50%; [L] is the concentration of $[^{125}I]$-MVIIA (SNX-111) OCT used in the experiment; and $K_d$ is the binding constant determined for binding of $[^{125}I]$-MVIIA (SNX-111) OCT to rat brain synaptosomal membranes in saturation binding experiments. Table 2 summarizes computed $IC_{50}$ for various omega-conopeptides for the MVIIA binding site of rat brain synaptosomal membranes.

Relative potency for displacement of binding is calculated as a ratio of the $IC_{50}$ of the test compound and the $IC_{50}$ of the reference compound. The reference compound is generally the unlabeled equivalent of the labeled ligand. Calculation of relative potency is as follows:

$$[log\ (relative\ potency)] = log\ (IC_{50(ref)}) = log(IC_{50(test)})$$

Relative potency values for binding at OCT MVIIA (SNX-111) and OCT SVIB (SNX-183) sites are listed in Table 3.

EXAMPLE 4

Crosslinking of $[^{125}I]$-SNX-111 and $[^{125}I]$-SNX-183 to Their Polypeptide Receptors A. SDS-gel electrophoretic analysis of rat hippocampal synaptosomal membrane polypeptides chemically crosslinked with A. $[^{125}I]$-SNX-111 and B. $[^{125}I]$-SNX-183 (FIG. 10). Both radioactive ligands (1 nM) were incubated with rat hippocampal synaptosomal membranes in the absence (middle lanes) or presence (right lanes) of excess non-radioactive peptide at 1000 times the $IC_{50}$ for binding (i.e., 10 nM for SNX-111 and 1 mM for SNX-183) and crosslinking was achieved by the addition of sulfo-N-hydroxysuccinimide (NHS) and the water-soluble carbodiimide, EDC (45). The left lanes are controls to which EDC and NHS were not added.

Figure 11B:
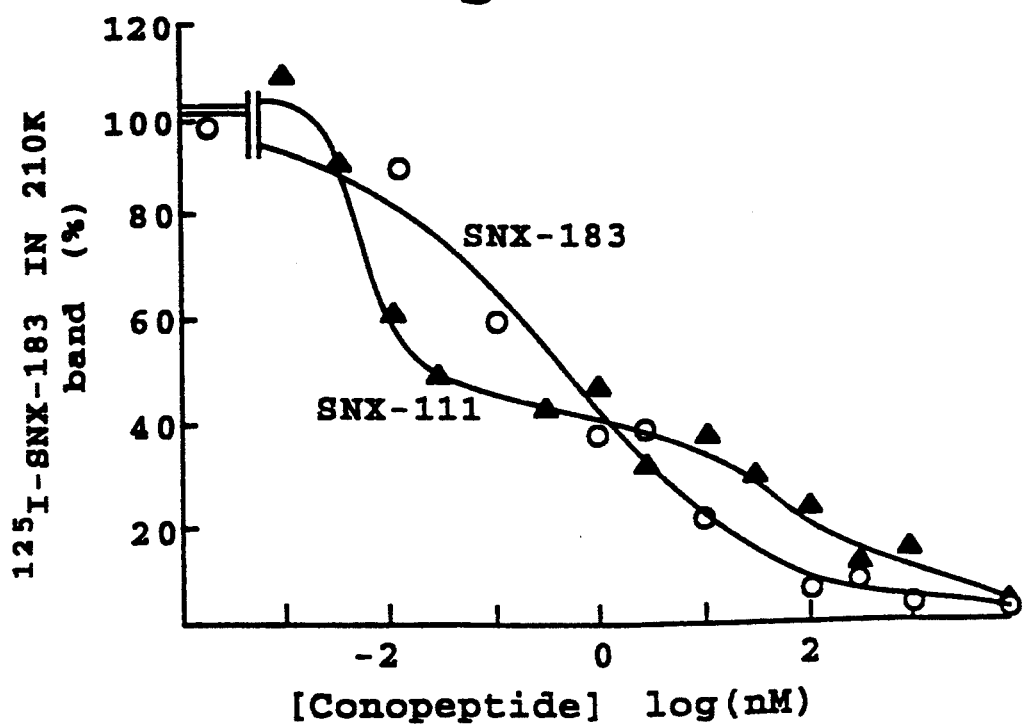
Figure 12E:
Figure 12F:
Figure 12G:
Figure 12H:

B. Displacement of crosslinked $^{125}I$-SNX-183 by SNX-111 $[^{125}I]$-SNX-111 (A) or $[^{125}I]$-SNX-183 (B) crosslinked to the 210 kDa polypeptide(s) in rat hippocampal synaptosomal membranes were displaced by increasing concentrations of non-radioactive SNX-111 and SNX-183 (FIG. 11A). As expected, the site 1-specific ligand $[^{125}I]$-SNX-111 was displaced monotonically by both SNX-111 and SNX-183. In contrast, displacement of $[^{125}I]$-SNX-183 by SNX-111 is biphasic with IC50's similar to its IC50's for binding to site 1 and site 2 (FIG. 11B). The amount of radioiodinated peptide incorporated into the 210 kDa band of crosslinked hippocampal synaptosomal membranes exposed to varying concentrations of competing peptides was estimated by scanning densitometry. The optical density of the 210 kDa band in the sample without added competing peptide was taken as 100%. Curves were fit to the data as described above.

EXAMPLE 5

Localization of OCT Binding Sites in Neuronal Tissue by Receptor Autoradiography Adult male (Fischer or Sprague-Dawley, 250–300 g) were euthanized with carbon-dioxide, and whole brains were dissected out of the skull and rapidly frozen in iso-pentane pre-cooled on frozen carbon dioxide. The frozen brains were stored at $-80°$ C. and used within a week.

Coronal sections (20$\mu$ thick) were obtained by slicing (at $-10°$ C. to $-15°$ C.) through the frozen brain using a cryostat microtome. The sections were thaw-transferred onto glass slides precoated with gelatin. Glass slides with the frozen sections were stored at $-80°$ C. and used within a week. Binding of $[^{125}I]$MVIIA was performed at room temperature. Each brain section was incubated for 40 min. with 250 $\mu$l of binding buffer: (HEPES/NaOH (20 mM, pH 7.5), EDTA (0.1 mM), EDTA (0.1 mm) leupeptin (2 $\mu$M), Aprotinin (0.63 mg/ml), 1.5% BSA (RIA Grade), and $[^{125}I]$MVIIA (100–150 pM). To determine the proportion of non-specific binding selected adjacent brain sections were incubated with an excess of unlabelled peptide (25 nm).

After the incubation, binding buffer was carefully poured onto blotting paper and the slides transferred to a glass slide holder. Unbound $[^{125}I]$MVIIA was washed away by serially passing the slides through four dishes of washing buffer at room temperature for a total washing time of 16 min. Washing buffer contained HEPES/-NaCH (50 ml9, pH 7.5), NaCl (170 mM), BSA (RIA grade lg/L) and Triton X-100 (0.05%). After the final wash, the slides were dipped quickly five times in water and dried with a blow-dryer.

Dried slides were exposed to XAR-2 film, overnight at room temperature and developed. The developed images were examined wither directly or by computer assisted image analyzer. The assignment of binding to specific neuroanatomical sites was made using an anatomical atlas of rat brain (Paxinos).

Autoradiograms show the distributions of [$^{125}$I]-SNX-111 (A,B,C,D) and [$^{125}$I]-SNX-183 (E,F,G,H) (FIG. 12) binding to coronal rat brain sections. Labeling in the presence of excess non-radioactive SNX-111 (C,D) or SNX-183 (G,H) shows that non-specific labeling is negligible. Rostral sections (A,C,E,G) and caudal sections (B,D,F,H) are each adjacent or near-adjacent. "CA" indicates the $CA_3$ region of the hippocampus and "SN" indicates the substantia nigra.

EXAMPLE 6

Inhibition of Neurotransmitter Release

A. Inhibition of Norepinephrine Release

Inhibitory constants (IC50's) reflecting the potency of SNX-111 and SNX-183, for blocking the K+-evoked release of exogenous, loaded [$^3$H]-norepinephrine from rat hippocampal slices were determined. Freshly dissected hippocampal slices in oxygenated buffered saline were loaded with [3H]-norepinephrine and washed three times. Slices were then exposed to buffered saline (containing 3.3 mM K+) for 1.5 minutes and the supernatants containing released basal norepinephrine were collected for scintillation counting. The slices were then depolarized by exposure to buffered saline containing 30 mM K+ for 1.5 minutes and the supernatants, containing evoked norepinephrine, were also collected for scintillation counting. Slices were exposed to the desired concentration of peptide in all solutions from the time of loading with norepinephrine to the end of the experiment (about 2 hours). The data points are the differences of the means of 7 basal determinations and 7 evoked determinations at each drug concentration. Release in the absence of drug is taken as 100 per cent and the remaining points are scaled accordingly (FIG. 13A). The error bars are the standard errors of the means of the differences. Curves of best fit and the corresponding IC50's were derived. The single IC50 for SNX-111 is correlated with binding to site 1 calcium channels; the two IC50s for SNX-230 are for inhibition associated with binding to site 1 calcium channels (65 nM) and to site 2 calcium channels (0.02 nM); the apparent single IC50 for SNX-183 is presumed to reflect binding to both site 1 and site 2 calcium channels with about equal affinity (see text). Evoked release in the absence of Ca++ in the buffer was equal to basal release (data not shown); thus all release shown is calcium-dependent release.

B. Inhibition of ATP Release from Electric Organ Synaptosomes

Synaptosomes were prepared substantially as described in Example 2A. The diluted synaptosome suspension from the final centrifugation step was pelleted at 30,400 x g for 15 min and resuspended in 1 ml of synaptosome buffer (with the inclusion, for some experiments, of 1% BSA to enhance stability of the synaptosomes). This final synaptosome preparation was stored at 0° C. and used for ATP release experiments within 30 hours. Storage for longer periods resulted in the almost complete loss of depolarization-dependent ATP release activity.

Luminometry was performed according to published methods (Ahmad, Miljanich). Into a 5 ml polypropylene test tube were mixed 465 μl synaptosome buffer, 5 μl of 5 μg/ml luciferin in PSB, 20 μl firefly lantern extract (1 Sigma FLE-50 bottle reconstituted in 1 ml PSB and spin-dialyzed through 3 ml of Sephadex G-25 pre-equilibrated in PSB), 5 μl 100 mM $CaCl_2$, and 5 μl synaptosome suspension (5-7 mg/ml protein, excluding BSA). The tube was placed in the chamber of a custom-built luminometer and the light output produced by extracellular ATP was continuously monitored by a chart recording of the voltage generated by the photomultiplier tube. Exocytotic release of ATP was evoked by injecting 0.5 ml of high K+ buffer (synaptosome buffer with equimolar replacement of Na+ by K+) into the reaction mixture in the luminometer.

ATP release was quantitated by comparing the peak heights of unknowns with the heights of peaks generated by ATP standards that were injected into each reaction mixture at the end of each trial. Over the range investigated, light output was linear with respect to the amount of ATP injected. $IC_{50}$ values were calculated from the dose-dependent ATP inhibition curves, and are reported in Table 6.

C. Inhibition of Dopamine Release from Rat Striatal Slices

Slices (0.3×0.3×1.5 mm) were prepared from rat striatum, and were pre-loaded with radiolabeled (tritiated) dopamine. Slices were perfused for 45 minutes in Krebs Ringer Bicarbonate buffer (oxygenated) as bathing medium. Release of neurotransmitter was stimulated by adding to the perfusion medium KCl at a concentration ranging between 4.8 and 15 mM, for a period of one minute. The first such exposure was termed S1. Perfusion with bathing medium was continued. Test compound(s) were introduced into the perfusion medium 20 minutes before the second stimulation (S2), which was done identically to S1. The ratio of S2/S1 was calculated to determine drug effects. A drug was considered to block release if S2/S1 was significantly less than unity.

D. Inhibition of Acetylcholine Release from Striatal Slices

Release of acetylcholine was measured as described above in part C for dopamine release, except that slices were pre-loaded with radiolabelled choline instead of dopamine.

E. Inhibition of Electrically Stimulated Contractions of Guinea Pig Ileum

Guinea pigs (300-400 gms) were decapitated and the ileum removed. A section of ileum about 6 cm from the caecum was placed immediately into Krebb's modified buffer maintained at 37° C. in a water bath, and aerated with a mixture of 95% $O_2$ and 5% $CO_2$. The buffer contains: KCl, 4.6 mM; $KH_2PO_4$, 1.2 mM; $MgSO_4$, 1.2 mM; Glucose, 10.0 mM; NaCl 118.2 mM; $NaHCO_3$, 24.8 mM; $CaCl_2$, 2.5 mM.

Small pieces of ileum were cut and pulled over a glass pipette, scored and the longitudinal muscle removed. Each piece was attached to an electrode at one end and to a force transducer at the other end. The preparation was lowered into an organ bath maintained at 37° C. and aerated with $O_2:CO_2$. The resting tension was set at 1 gm, and the tissue was stimulated at 30–50V with a duration of 4.5 msec per stimulation.

Baseline responses (contractions) were recorded for 10–15 min. and aliquots (100 ml) of drug were added to the bath until inhibition occurred. Following testing, tissues were washed until original response magnitude was achieved.

F. Inhibition of Amino Acid Neurotransmitter Release from Rat Brain Slices

Male Sprague-Dawley rats were lightly anesthetized with ether, decapitated, and the brains removed to ice cold oxygenated basal medium (in mM: NaCl; 118, KCl, 4.8; $CaCl_2$, 1.3; $MgSO_4$, 1.2; $KH_2PO_4$, 1.2; glucose, 11). Hippocampus and cerebral cortex were further dissected from the brain and slices (300–400 μm thick) were prepared using a γ McIlwain Tissue Chopper at 4 degrees. Each slice was preincubated at 37 degrees for 15 minutes. Buffer was then replaced with an equal volume of either basal medium or stimulation medium (in mM: NaCl; 88, KCl, 30; $CaCl_2$, 1.3; $MgSO_4$, 1.2; $KH_2PO_4$, 1.2; glucose, 11). Incubation was then continued for 15 minutes. Tubes containing slices were then centrifuged for 1 minute in a Beckman Microfuge. The supernatants were collected and heated for 10 minutes at 100 degrees. Aliquots (20 ul) were used for analysis of amino acid content using pre-column derivatization with o-phthalaldehyde followed by HPLC as described by Newcomb.

Table 7 shows the effect of MVIIA OCT on K-stimulated release of amino acid neurotransmitters (Aspartate, GABA, glutamate). Significant reductions in the amount of GABA and glutamate were observed, as reported in Table 7.

EXAMPLE 7

Rat Tail-Flick Assay for Analgesia

Male Sprague-Dawley rats (250–300 g; Simonsen) were implanted with intrathecal (i.t.) catheters, which were inserted through the atlanto-occipital membrane and threaded subdurally about 8 cm therefrom. Animals were not used in experiments until at least 2 days following implantation.

To perform the Tail-Flick test, a rat was restrained in a plastic cone having openings at each end, and was placed on a platform, positioned such that its tail hung down from the platform in close proximity to a heating bulb. Latency to flick the tail away from the bulb was recorded. A trial consisted of four such flicks at 1–2 min. intervals, where the first latency time was generally not used, and the three subsequent tests were averaged. Latencies measured in the absence of analgesic agent(s) were recorded for each rat as "Baseline latency."

Rats were then removed from the restraining cones, and injected (i.t.) with test compound in a volume of 5 μl, followed by 10 μl saline. Animals were subjected to post-drug trials at one or more time intervals thereafter (usually 25 min and 45 min.), as described above. In the cases where drug enhancement was tested, test compound was first injected, followed by tail-flick trials, to assess the potency of the drug alone. Approximately 1 hour later, a known analgesic, such as morphine, was injected, and trials repeated.

Drug effects were calculated as follows:

$$\% \text{ Effect} = 100 \times \frac{\text{(post-drug latency)} - \text{(baseline latency)}}{\text{(maximum latency)} - \text{(baseline latency)}},$$

where maximum latency was measured as experimental cut-off time, the time beyond which the tail was not allowed by the experimenter to be exposed to heat, due to risk of burn to the animal.

EXAMPLE 8

Rat Formalin Test for Analgesia

Rats (male Sprague-Dawley, 275–300 g) were implanted with lumbar intrathecal catheters under halothane anesthesia. Catheters extended from the cisterna to the rostral edge of the lumbar enlargement. 3–5 days after implant, animals without motor dysfunction were used.

Animals were examined for the effects of drugs given in the formalin test, in which 50 ul of 5% formalin was injected on the plantar surface of the paw. The number of flexions of the paw were counted at intervals after the injection of the formalin. Drugs tested in this assay were dissolved in sterile saline (0.9% NaCl) and injected in a volume of 10 ul followed by 10 ul to clear the catheter.

Injection of formalin alone or with vehicle (saline) resulted in a biphasic response pattern of hind paw withdrawals (see FIG. 16). The area under the curve of the flinches/min was calculated for phase 1 (time=0–10 min) and phase 2 (10–60 min). These values were plotted versus the intrathecal log dose (ug) and the results were plotted in FIG. 17.

Although the invention has been described with respect to particular embodiments, it will be apparent to those skilled that various changes and modifications can be made without departing from the invention.

It is claimed:

1. A method of producing analgesia in a mammalian subject, comprising
    administering to the subject, in the absence of an opiate, an omega conopeptide selected from the group consisting of TVIA (SNX-185), MVIIA (SNX-111) and derivatives thereof, wherein said omega conopeptide is effective (a) to inhibit electrically stimulated contraction of the guinea pig ileum, and (b) to bind selectively to omega conopeptide MVIIA binding sites present in neuronal tissue.

2. The method of claim 1, wherein the activities of the omega-conopeptide in calcium channel inhibition and in binding to the MVIIA binding site are within the ranges of such activities of omega-conopeptides MVIIA and TVIA.

3. The method of claim 1, wherein the omega-conopeptide is MVIIA or TVIA.

4. The method of claim 1, wherein the omega-conopeptide is administered intrathecally.

* * * * *

UNITED STATES PATENT AND TRADEMARK OFFICE
Certificate

Patent No. 5,364,842                                                  Patented: November 15, 1994

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Alan Justice, Sunnyvale, CA; Tejinder Singh, Palo Alto, CA; Kishorchandra Gohil, Richmond, CA; Karen L. Valentino, San Carlos, CA; and George P. Miljanich, Redwood City, CA.

Signed and Sealed this Thirtieth Day of September 2003.

<div align="right">
WILLIAM R. DIXON, JR.<br>
<em>Supervisory Patent Examiner</em><br>
Art Unit 1600
</div>